(12) United States Patent
Qu et al.

(10) Patent No.: US 12,377,160 B2
(45) Date of Patent: Aug. 5, 2025

(54) HUMANIZED ANTI-TISSUE FACTOR ANTIBODY, ANTIBODY-DRUG CONJUGATE PREPARED THEREFROM AND USE THEREOF

(71) Applicant: NANOLATTIX BIOTECHNOLOGY CO., LTD., Taiyuan (CN)

(72) Inventors: Zhican Qu, Taiyuan (CN); Yi Zhao, Taiyuan (CN); Xin Yang, Taiyuan (CN); Quanai Zhang, Taiyuan (CN); Weiwei Pan, Taiyuan (CN); Xinxin Liang, Taiyuan (CN); Jianli Li, Taiyuan (CN); Huahua Hao, Taiyuan (CN)

(73) Assignee: NANOLATTIX BIOTECHNOLOGY CO., LTD., Taiyuan (CN)

( * ) Notice: Subject to any disclaimer, the term of this patent is extended or adjusted under 35 U.S.C. 154(b) by 0 days.

(21) Appl. No.: 19/043,567

(22) Filed: Feb. 3, 2025

(65) Prior Publication Data
US 2025/0170257 A1     May 29, 2025

Related U.S. Application Data

(63) Continuation of application No. PCT/CN2024/071758, filed on Jan. 11, 2024.

(30) Foreign Application Priority Data

Mar. 24, 2023    (CN) .................. 202310308580.X

(51) Int. Cl.
  *A61K 47/68*   (2017.01)
  *A61P 35/00*   (2006.01)
  *C07K 16/36*   (2006.01)

(52) U.S. Cl.
  CPC .... *A61K 47/68031* (2023.08); *A61K 47/6843* (2017.08); *A61P 35/00* (2018.01);
  (Continued)

(58) Field of Classification Search
  None
  See application file for complete search history.

(56) References Cited

U.S. PATENT DOCUMENTS

2023/0027495 A1*   1/2023   Rangwala .......... A61K 47/6889

FOREIGN PATENT DOCUMENTS

| CN | 103342752 A | 10/2013 |
|----|-------------|---------|
| CN | 106467574 A | 3/2017  |

(Continued)

OTHER PUBLICATIONS

First Office Action for CN Application No. 202310308580.X, dated Nov. 15, 2023.

(Continued)

*Primary Examiner* — Daniel E Kolker
*Assistant Examiner* — Hilary Ann Petrash
(74) *Attorney, Agent, or Firm* — Troutman Pepper Locke LLP (Rochester)

(57) ABSTRACT

Provided is a humanized anti-tissue factor antibody, an antibody-drug conjugate prepared therefrom and use thereof. The humanized anti-tissue factor antibody has high affinity to tissue factor. Also provided is an antibody-drug conjugate, which is obtained by coupling the humanized anti-tissue factor antibody to a cytotoxic drug. Based on the humanized anti-tissue factor antibody, which has high affinity and short endocytosis time for tumor cells with low-and high-expression of tissue factor, the antibody-drug conjugate can quickly reach the target site of the tumor and exert a cytotoxic effect. The humanized anti-tissue factor antibody can effectively inhibit the growth of tumor cells and the growth of subcutaneous tumors in mice. Therefore, the antibody-drug conjugate of the present disclosure plays an important role in cancer therapy.

10 Claims, 11 Drawing Sheets
Specification includes a Sequence Listing.

(52) U.S. Cl.
CPC .......... *C07K 16/36* (2013.01); *C07K 2317/24* (2013.01); *C07K 2317/732* (2013.01); *C07K 2317/92* (2013.01)

(56) References Cited

FOREIGN PATENT DOCUMENTS

| | | |
|---|---|---|
| CN | 106938051 A | 7/2017 |
| CN | 107446047 A | 12/2017 |
| CN | 110575547 A | 12/2019 |
| CN | 116789837 A | 9/2023 |
| WO | 2019102435 A1 | 5/2019 |

OTHER PUBLICATIONS

International Search Report for PCT/CN2024/071758, dated Apr. 22, 2024.

\* cited by examiner

HUMANIZED ANTI-TISSUE FACTOR ANTIBODY, ANTIBODY-DRUG CONJUGATE PREPARED THEREFROM AND USE THEREOF

CROSS-REFERENCE TO RELATED APPLICATION

This patent application is a continuation application of International Patent Application No. PCT/CN2024/071758, filed on Jan. 11, 2024, which claims the benefit and priority of Chinese Patent Application No. 202310308580X filed with the China National Intellectual Property Administration on Mar. 24, 2023, the disclosure of which is incorporated by reference herein in its entirety as part of the present application.

REFERENCE TO SEQUENCE LISTING

A computer readable XML file entitled "GWPCTP20241207826-sequence listing", which was created on Jan. 17, 2025, with a file size of about 59,872 bytes, contains the sequence listing for this application, has been filed with this application, and is hereby incorporated by reference in its entirety.

TECHNICAL FIELD

The present disclosure belongs to the technical field of biopharmaceutical technology and specifically relates to a humanized antibody to anti-tissue factor, an antibody-drug conjugate prepared therefrom and use thereof.

BACKGROUND

Antibody-drug conjugate (ADC) consists of three parts: a monoclonal antibody, a cytotoxic drug, and a linker. The advantage of ADCs is that they utilize the targeting properties of antibody drugs to precisely direct small molecule cytotoxic drugs to tumor tissues, release highly active cytotoxins, and kill tumor cells, which effectively improve the targeting of anti-tumor drugs. At the same time, the ADC drugs can accurately recognize the target and does not affect normal non-cancer cells, which greatly reduces the toxic and side effects of tumor chemotherapy. In recent years, precisely because the ADC drugs combine the powerful killing effect of traditional small molecule chemotherapy and the tumor targeting of antibody drugs, they have always been a research hotspot in the field of precision tumor treatment and have gradually become a hot field for new drug research and development.

Tissue factor (TF) is a transmembrane protein with a molecular weight of 47 kDa that initiates the exogenous blood coagulation pathway. However, it has been reported in a series of scientific research in recent years that tissue factor is abnormally expressed to varying degrees in a variety of tumor cells, and the expression of tumor tissue factors is positively correlated with the degree of tumor malignancy. For example, the positive rate of pancreatic cancer and cervical cancer is 100%. The positive rate is 34%-88% for non-small cell lung cancer, 14%-100% for endometrial cancer, 47%-75% for prostate cancer, 75%-100% for ovarian cancer, 43%-91% for esophageal cancer, and 50%-78% for bladder cancer. The abnormally high expression of tissue factor in these tumors leads to an increase in coagulation activity in tumor tissues and blood vessels and to enhanced adhesion of tumor cells, which promotes the migration and escape of tumor cells that invade blood vessels. In tumor cells, intracellular signal transduction promotes VEGF transcription, inducing tumor angiogenesis. The high expression of tissue factor is closely related to tumor growth, angiogenesis, metastasis and clinical treatment, and the development of tumor treatment drugs targeting tissue factor has gradually become a hot spot in the industry.

However, there are very limited reports on monoclonal antibodies targeting tissue factors in the prior art, and the affinity of monoclonal antibodies is not ideal, which undoubtedly hinders the research and development of antibody-drug conjugates that target tissue factor.

SUMMARY

In view of this, an object of the present disclosure is to provide a humanized anti-tissue factor antibody with high affinity to tissue factor.

Another object of the present disclosure is to provide an antibody-drug conjugate, which is formed by coupling a humanized anti-tissue factor antibody and a cytotoxic drug. The antibody-drug conjugate has the characteristics of short endocytosis time and high affinity for tumor cell strains with low tissue factor expression, thus playing an important role in tumor or cancer therapy.

The present disclosure provides a humanized anti-tissue factor antibody, where the humanized anti-tissue factor antibody includes a heavy chain having the amino acid sequence set forth in SEQ ID NO: 3, and the humanized anti-tissue factor antibody includes a light chain having the amino acid sequence set forth in SEQ ID NO: 4.

The present disclosure provides an antibody-drug conjugate obtained by coupling the humanized anti-tissue factor antibody with a cytotoxic drug.

Preferably, the cytotoxic drug is at least one selected from the group consisting of a dolastatin derivative such as monomethyl auristatin E (MMAE), an anti-tubulin inhibitor such as monomethyl auristatin F (MMAF), a maytansinoid derivative such as DM1, and a DNA topoisomerase I inhibitor such as DX8951.

Preferably, the humanized anti-tissue factor antibody and the cytotoxic drug are coupled via a linker, where the linker is at least one selected from the group consisting of GGFG four-peptide linker, valine-citrulline dipeptide linker, and SMCC thioether linker;

a linker-cytotoxic drug is selected from the group consisting of MC-VC-PAB-MMAE, MC-VC-PAB-MMAF, MC-VC-PAB-DM1, MC-GGFG-DX8951, MC-SMCC-DM1;

where a DAR value of the antibody-drug conjugate is 2-8.

The present disclosure provides a method for preparing the antibody-drug conjugate, including the following steps:

mixing the humanized anti-tissue factor antibody and tris(2-chloroethyl) phosphate with conjugation buffer for reduction reaction to obtain a reduced product; and coupling the reduced product to the linker-cytotoxic drug in a solution of the linker-cytotoxic drug to obtain the antibody-drug conjugate.

Preferably, a mass-volume ratio of the humanized anti-tissue factor antibody to tris(2-chloroethyl) phosphate is (1-2):(2-3).

A mass ratio of the humanized anti-tissue factor antibody to the linker-cytotoxic drug is 1:(5-9).

Preferably, a temperature for the reduction reaction is 23-27° C., and a time for the reduction reaction is 1-2 h.

A temperature for the coupling reaction is 23-27° C.; and a time for the coupling reaction is 1-2 h.

The present disclosure also provides a single-chain fusion protein formed by a heavy chain variable region and a light chain variable region of the humanized anti-tissue factor antibody, and a reporter protein;
where the amino acid sequence of the heavy chain variable region of the humanized anti-tissue factor antibody is set forth in SEQ ID NO: 47;
and the amino acid sequence of the light chain variable region of the humanized anti-tissue factor antibody is set forth in SEQ ID NO: 48.

The present disclosure provides use of the single-chain fusion protein in detecting the expression of tissue factor on surface of tumor cells.

The present disclosure provides use of the antibody-drug conjugate in preparation of a drug for treating cancer.

The present disclosure provides use of the antibody-drug conjugate in the preparation of a drug for treating cancer in combination with an additional anti-cancer drug.

Preferably, the cancer is a cancer with abnormal tissue factor expression, and the cancer with abnormal tissue factor expression is at least one selected from the group consisting of ovarian cancer, non-small cell lung cancer, in-situ adenocarcinoma, colon cancer, cervical cancer, prostate cancer, endometrial cancer, pancreatic cancer, esophageal cancer, bladder cancer, gastric cancer, liver cancer, and breast cancer.

The present disclosure provides a humanized anti-tissue factor antibody, where the humanized anti-tissue factor antibody includes a heavy chain having the amino acid sequence set forth in SEQ ID NO: 1, and the humanized anti-tissue factor antibody comprises a light chain having the amino acid sequence set forth in SEQ ID NO: 2. In the present disclosure, the hybridoma cells prepared by immunizing an animal with the tissue factor are screened for affinity to obtain two hybridoma cell strains with relatively strong affinity, and two anti-tissue-factor antibodies secreted by the two hybridoma cell strains are subjected to humanization and recombinant expression to obtain a humanized antibody that specifically binds to the tissue factor. Through surface plasmon resonance (SPR) detection, the humanized antibody according to the present disclosure is determined to have higher affinity, while the other humanized antibody has lower affinity. In the examples of the present disclosure, the affinity kinetic analysis experiments show that KD of humanized antibody MAb01 according to the present disclosure with tissue factor is $3.57 \times 10^{-10}$ M, while KD of the other humanized antibody MAb02 is $1.002 \times 10^{-9}$ M. In summary, the high affinity humanized anti-tissue factor antibody has stronger affinity to the antigen tissue factor.

The present disclosure provides an antibody-drug conjugate obtained by coupling the humanized anti-tissue factor antibody with a cytotoxic drug. The Cell endocytosis experiments show that two humanized anti-tissue factor antibodies with different affinities are prepared into antibody-drug conjugates. The obtained antibody-drug conjugates are subjected to fluorescence labeling with fluorescein isothiocyanate (FITC) and separately detected in tumor cells with high-expression of tissue factor and low expression of tissue factor. The results showed that antibody-drug conjugates including humanized anti-tissue factor antibodies with high affinity are internalized in tumor cells with low expression of tissue factor, which may greatly promote preclinical development, clinical transformation and treatment effects in patients. At the same time, cell-level biological activity detection experiments show that the antibody-drug conjugate prepared in the present disclosure may inhibit the biological activity of tumor cells with low or high expression of tissue factor. In addition, animal experiments show that the antibody-drug conjugate prepared in the present disclosure may effectively inhibit tumor growth. It can be seen that the antibody-drug conjugate provided in the present disclosure can not only inhibit the growth of tumors with high expression of tissue factor, but also effectively inhibit the growth of tumors with low expression of tissue factor, providing a general drug for the treatment of various tumors or cancers, which has great value in clinical application.

DETAILED DESCRIPTION OF THE EMBODIMENTS

Figure 1:
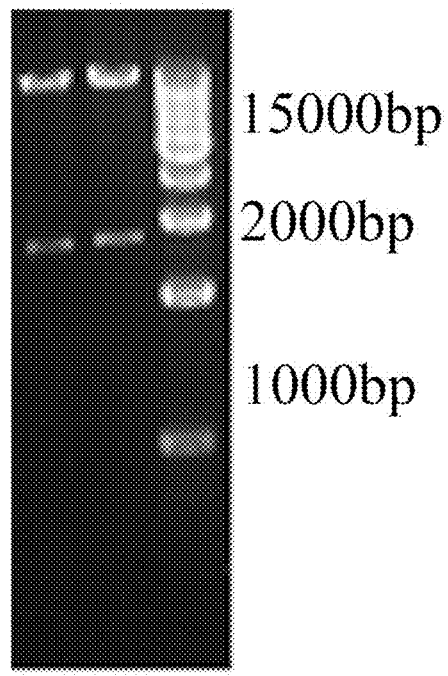
FIG. 1 shows the verification results of the recombinant vector for expressing humanized anti-tissue factor antibody.

The present disclosure provides a humanized anti-tissue factor antibody, and the amino acid sequence of heavy chain (HC) of the humanized anti-tissue factor antibody is shown in SEQ ID NO: 3 (QIQLVQSGPELVKPGASVQVSCK-TSGYSFTDYNVYWVRQSPAKGIEWIGYIDPYN GLTI-YEQNFRGKGTLSLDHSTSTAYMELNSLRYEDTAVY-FCARDVTTALDFWGQGTSVTVSS EFASTKGPSVFPL-APSSKSTSGGTAALGCLVKDYFPEPVTVSWNSGALT-SGVHTFPAVLQSSG LYSLSSVVTVPSSSLGTQTYIC-NVNHKPSNTKVDKKVEPKSCDKTHTCPPCPAPELL- GGPSVF LFPPKPKDTLMISRTPEVTCVVVDVS HEDPEVKFNWYVDGVEVHNAKTKPREEQYNSTYRV VSVLTVLHQDWLNGKEYKCKVSNKALPAPIEKTISK AKGQPREPQVYTLPPSRDELTKNQVS LTCLVKGF YPSDIAVEWESNGQPENNYKTTPPVLDSDGSFFLY- SKLTVDKSRWQQGNVFSCS VMHEALHNHYTQ KSLSLSPGK), containing 449 amino acid residues; and the amino acid sequence of the light chain (LC) of the humanized anti-tissue factor antibody is set forth in SEQ ID NO: 4 (DIQMTQSPASISASIGERVTITCLASQTIDTWLAW-FLQKPGRSPNLLIYAATNLADGVPYRFS ASGSGND-FSLTISSLNPEDVATYYCQQVYSSPFTFGQGNKLEI RRTVAAPSVFIFPPSDEQLKS GTASVVCLLNNFYP REAKVQWKVDNALQSGNSQESVTEQDSKDSTYS-LSSTLTLSKADYEK HKVYACEVTHQGLS SPVTKSFNRGEC), containing 214 amino residues.

In the examples of the present disclosure, the screened two kinds of anti-tissue-factor monoclonal antibodies are humanized and recombinantly expressed to obtain two kinds of humanized anti-tissue factor antibodies. The results of affinity analysis show that the humanized anti-tissue factor antibody MAb01 according to the present disclosure has strong affinity and has the ability to specifically recognize tissue factor, which is significantly better than the other humanized anti-tissue factor antibody MAb01. The corresponding amino acid sequence of the heavy chain is SEQ ID NO: 1 (QIQLVQSGPEVVKPGASVRVSCKGSGYSFT-DYNIYWVRQSPAKGLE WIGYIDPYNGLTIYDQN-FRAKATLSVDHSTSNAYMEINSLRYEDTAVYFCA RDVTSALEFWG QGTSVTVSSEFASTKGPSVF-PLAPSSKSTSGGTAALGCLVKDYFPEPVTVSW NSGA LTSGVHT FPAVLQSSGLYSLSSVVTVPSSSLGTQTY ICN VNHKPSNTKVDKKVEPKSCDKTHTCPPCPAP ELLGGPSVFLFPPKPKDTLMISRTPEVTCVVVDV SHEDPEVKFNWYVDGVEVHNAKTKPRE EQYN-STYRVVSVLTVLHQDWLNGKEYKCKVSNKALPA-PIEKTISKAKGQPREPQVYTLPPSR DELTKNQVSLT-CLVKGFYPSDIAVEWESNGQPENNYKTTPPVLDSD-GSFFLYSKLTVDKSRW QQGNVFSCSVMHEALHN-HYTQKSLSLSPGK), and the corresponding amino acid sequence of the light chain is SEQ ID NO: 2 (DIQMTQSPA-SISASVGERVTITCLGSQTIDTYLAWYLQKPGRSP QLLIYAATQLADGVPSRFSASGSGTDFSLTISSLQPED-VATYYCQNVYSSPFTFGQGNKLEIKR TVAAPSVFI FPPSDEQLKSGTASVVCLLNNFYPREAKVQWKVD-NALQSGNSQESVTEQDSK DSTYSLSSTLTLSKAD YEKHKVYACEVTHQGLSSPVTKSFNRGEC).

The present disclosure provides an antibody-drug conjugate obtained by coupling the humanized anti-tissue factor antibody with a cytotoxic drug.

In the present disclosure, the cytotoxic drug is at least one selected from the group consisting of a dolastatin derivative such as MMAE, an anti-tubulin inhibitor such as MMAF, a maytansinoid derivative such as DM1, and a DNA topoisomerase I inhibitor such as DX8951. The humanized anti-tissue factor antibody and the cytotoxic drug are coupled by a linker. The linker is preferably at least one selected from GGFG four-peptide linker, valine-citrulline dipeptide linker, and SMCC thioether bond linker. The linker-cytotoxic drug is selected from the group consisting of MC-VC-PAB-MMAE, MC-VC-PAB-MMAF, MC-VC-PAB-DM1, MC-GGFG-DX8951, and MC-SMCC-DM1.

The present disclosure provides a method for preparing the antibody-drug conjugate, including the following steps:
mixing the humanized anti-tissue factor antibody and tris(2-chloroethyl) phosphate with conjugation buffer for reduction reaction to obtain a reduced product; and
coupling the reduced product to the linker-cytotoxic drug in a solution of the linker-cytotoxic drug to obtain the antibody-drug conjugate.

In the present disclosure, the mass volume ratio of the humanized anti-tissue factor antibody to tris(2-chloroethyl) phosphate is preferably (1-2):(2-3), more preferably 1:3; 1:2; 2:3, and most preferably 1:3. The temperature for the reduction reaction is preferably 23-27° C., more preferably 25° C. The time for the reduction reaction is preferably 1-2 h, more preferably 1.5 h. The DAR value of the antibody-drug conjugate is preferably 2 to 8, and more preferably 3.6 to 4.4.

In the present disclosure, the mass ratio of the humanized anti-tissue factor antibody to linker-cytotoxic drug is preferably 1:(5-9), more preferably 1:5, 1:6, 1:7, 1:8, 1:9, even more preferably 1:7. The temperature for the coupling reaction is preferably 23-27° C., more preferably 25° C. The time for the coupling reaction is preferably 1-2 h, more preferably 1.5 h.

The present disclosure provides a single-chain fusion protein, which is fusion protein formed by the heavy chain variable region and light chain variable region of the humanized anti-tissue factor antibody and a reporter protein; the amino acid sequence of the heavy chain variable region of the humanized anti-tissue factor antibody is set forth in SEQ ID NO: 47 (QIQLVQSGPELVKPGASVQVSCKTSGYS FTDYNVYWVRQSPAKGIEWIGYIDPYNGLTIYEQ NFRGKGTLSLDHSTSTAYMELNSLRYEDTAVYFCAR DVTTALDFWGQGTSVTVSS); and the amino acid sequence of the light chain variable region of the humanized anti-tissue factor antibody is set forth in SEQ ID NO: 48 (DIQMTQSPASISASIGERVTITCLASQTIDTWLAWFLQ KPGRSPNLLIYAATNLADGVPYRFSASGSGNDFSL TISSLNPEDVATYYCQQVYSSPFTFGQG NKLEIR).

In the present disclosure, there is no special limitation on the type of the reporter protein, and any type of reporter protein well known in the art, for example, green fluorescent protein, can be used. In the examples of the present disclosure, the amino acid sequence of the single-chain fusion protein is set forth in SEQ ID NO: 5, and the nucleotide sequence of the gene encoding the single-chain fusion protein is set forth in SEQ ID NO: 6. In the present disclosure, there is no special limitation on the method for expressing the fusion protein, and the method for preparing recombinant expression proteins well known in the art can be used.

The present disclosure provides use of the single-chain fusion protein in detecting the expression of tissue factor on the surface of tumor cells.

In the present disclosure, the method for detecting the expression of tissue factor on the surface of tumor cells preferably includes steps of: adding tumor cells to a black ELISA detection plate coated with tissue factor protein, incubating the tumor cells, washing the plate, and then adding single-chain fusion protein to incubate the single-chain fusion protein, and washing the plate; then adding a buffer solution to resuspend, and testing the resulting solution on the instrument at an excitation wavelength of 493 nm and an emission wavelength of 528 nm to obtain the absorbance value; and calculating the expression level of tissue factor on the surface of tumor cells based on a regression equation obtained from the standard curve. The solution used for washing is preferably a phosphate buffer saline (PBS) solution. The buffer used for resuspension is preferably a PBS solution. The time for the incubation is preferably 1-1.5 h. The results show that SK-OV-3 and BXPC-3 cell strains has the highest expression levels of tissue factor on the surface, while the SW620 and A549 cell strains has the lowest expression levels of tissue factor on the surface. The present disclosure provides a method that allows for calculating the number of targets for tissue factor on the surface of each type of tumor cells, thereby providing guidance for administration of the antibody-drug conjugate.

In the present disclosure, the antibody-drug conjugate prepared in the present disclosure is based on the high affinity to the tissue factor possessed by the humanized anti-tissue factor antibody and has a short endocytosis time, ensuring that the conjugated cytotoxin can quickly reach the tumor cells to produce cytotoxicity or cell killing effect. At the same time, given that the humanized anti-tissue factor antibody has a high affinity to tumor cells with low expression of tissue factor; it is guaranteed that tumor types with low expression of tissue factor are also suitable for the treatment with the antibody-drug conjugate. Experiments have shown that the antibody-drug conjugate can effectively inhibit the growth of tumor cells and the growth of subcutaneous tumors in mice, thereby playing an important role in the treatment of various cancer diseases. In view of this, the present disclosure provides the use of the antibody-drug conjugate in the preparation of a drug for cancer treatment. The present disclosure provides the use of the antibody-drug conjugate in the preparation of a drug for cancer treatment in combination with an additional anti-cancer drug. The mass ratio of the antibody-drug conjugate to the additional anti-cancer drug is 1:(23-27), more preferably 1:25. The additional anti-cancer drug preferably includes gemcitabine.

In the present disclosure, the cancer is a cancer with abnormal tissue factor expression. the cancer with abnormal tissue factor expression is preferably at least one selected from the group of consisting of: ovarian cancer, non-small cell lung cancer, in-situ adenocarcinoma, colon cancer, cervical cancer, prostate cancer, endometrial cancer, pancreatic cancer, esophageal cancer, bladder cancer, gastric cancer, liver cancer, and breast cancer.

The humanized anti-tissue factor antibody provided in the present disclosure, an antibody-drug conjugate prepared therefrom and its use will be described in detail below with reference to examples. However, these examples should not be understood as limiting the scope of protection of the present disclosure.

Example 1

Sequence Modification Experiment of Humanized Anti-Tissue Factor Antibody

The humanized antibody against tissue factor disclosed in a previous patent application by the instant applicant (publication No.: CN 107446047A) was artificially modified. The software Discovery Studio™ was used to mutate the virtual amino acids of the humanized antibody based on interactions to improve the binding affinity of the antibody. This modification resulted in two sequences of humanized anti-tissue factor antibody MAb01 and MAb02, and the modified sequences are shown in Table 1 and Table 2.

TABLE 1

Variable region of the heavy chain

| Region | Sequence before modification | MAb01 | MAb02 |
| --- | --- | --- | --- |
| FR1 | EVQLQQSGPELVKPGASVKVSCKASGYTFT (SEQ ID NO: 7) | QIQLVQSGPELVKPGASVQV SCKTSGYSFT (SEQ ID NO: 8) | QIQLVQSGPEVVKPGASVRVSCKGSGYSFT (SEQ ID NO: 9) |
| CDR1 | HFNVY (SEQ ID NO: 10) | DYNVY (SEQ ID NO: 11) | DYNIY (SEQ ID NO: 12) |
| FR2 | WVRQSPGKGLEWIG (SEQ ID NO: 13) | WVRQSPAKGIEWIG (SEQ ID NO: 14) | WVRQSPAKGLEWIG (SEQ ID NO: 15) |
| CDR2 | YIDPDNGITFYDENFM (SEQ ID NO: 16) | YIDPYNGLTIYEQNFR (SEQ ID NO: 17) | YIDPYNGLTIYDQNFR (SEQ ID NO: 18) |
| CDR3 | GKATLTVDKSSSTAYMQLNSLTSEDSAVYYCAR (SEQ ID NO: 19) | GKGTLSLDHSTSTAYMELNSLRYEDTAVYFCAR (SEQ ID NO: 20) | AKATLSVDHSTSNAYMEINSLRYEDTAVYFCAR (SEQ ID NO: 21) |
| FR3 | DVTTAVDF (SEQ ID NO: 22) | DVTTALDF (SEQ ID NO: 23) | DVTSALEF (SEQ ID NO: 24) |
| FR4 | WGQGTTLTVSS (SEQ ID NO: 25) | WGQGTSVTVSS (SEQ ID NO: 26) | WGQGTSVTVSS (SEQ ID NO: 26) |

TABLE 2

Variable region of Light chain

| | Original sequence | MAb01 | MAb02 |
| --- | --- | --- | --- |
| FR1 | DIQMTQSPSSLSASVGDRVTITC (SEQ ID NO: 27) | DIQMTQSPASISASIGERVTITC (SEQ ID NO: 28) | DIQMTQSPASISASVGERVTITC (SEQ ID NO: 29) |
| CDR1 | LATQTLDTWLA (SEQ ID NO: 30) | LASQTIDTWLA (SEQ ID NO: 31) | LGSQTIDTYLA (SEQ ID NO: 32) |

TABLE 2-continued

Variable region of Light chain

| | Original sequence | MAb01 | MAb02 |
|---|---|---|---|
| FR2 | WYQQKPGKAPQLLIY (SEQ ID NO: 33) | WFLQKP GRSPNLLIY (SEQ ID NO: 34) | WYLQKPGRSPQLLIY (SEQ ID NO: 35) |
| CDR2 | AATYLAD (SEQ ID NO: 36) | AATNLAD (SEQ ID NO: 37) | AATQLAD (SEQ ID NO: 38) |
| CDR3 | GVPSRFSGSGSGTDFTFT ISSLQPEDFATYYC (SEQ ID NO: 39) | GVPYRFSASGSGNDFSL TISSLNPEDVATYYC (SEQ ID NO: 40) | GVPSRFSASGSGTDFSLTISSL QPEDVATYYC (SEQ ID NO: 41) |
| FR3 | QLVYSSPST (SEQ ID NO: 42) | QQVYSSPFT (SEQ ID NO: 43) | QNVYSSPFT (SEQ ID NO: 44) |
| FR4 | FGQGTKLEIK (SEQ ID NO: 45) | FGQGNKLEIR (SEQ ID NO: 46) | FGQGNKLEIK (SEQ ID NO: 49) |

The heavy chain (HC) of the humanized anti-tissue factor antibody MAb02 was obtained, containing 449 amino acid residues set forth in SEQ ID NO: 1. The light chain (LC) contains 214 amino acid residues set forth in SEQ ID NO: 2. The heavy chain (HC) of humanized anti-tissue factor antibody MAb01 contains 449 amino acids set forth in SEQ ID NO: 3. The light chain gene (LC) contains 214 amino acids set forth in SEQ ID NO: 4.

Example 2

Expression of Humanized Anti-Tissue Factor Antibody and Screening of Stable Cell Strain The screening method in this example is consistent with that in the patent application (application publication number: CN 107446047A). After artificially synthesis of the genes encoding humanized antibodies MAb01 and MAb02, gene fragments of the heavy chain of MAb01 and MAb02, and pinsulator4X-MSA vector were double-digested separately with Sal I and Asc I. Electrophoresis was conducted using 1% agarose gel, the fragments of inserted fragment 1 (1425 bp) and the linearized vector 1 (11938 bp) were recovered from the gel, and the two fragments were ligated overnight at 4° C. to form a ligated product. At the same time, after the gene sequences of MAb01 and MAb02 light chain gene LC fragments were synthesized, Not I and Bci I were used to separately double-digest the gene fragments of the light chain of MAb01 as well as MAb02 and pCAGGS-IRES-AscI vector, electrophoresis and recovery of the insert fragment 2 (720 bp) and the linearized vector fragment 2 (6838 bp) from gel were carried out, and the two fragments were ligated overnight at 4° C. to form a ligated product. The ligated product was transformed into DH5a competent cells, and single colonies were screened with ampicillin. The single colonies were cultured at 37° C. overnight, and the plasmid was extracted from the bacteria and was verified through enzyme digestion methods.

After the above recombinant plasmid was verified, Sal I and MauB I were used to double-digest pinsulator4X-MAb01 heavy chain-dhfr and pinsulator4X-MAb02 heavy chain-dhfr. The enzyme digestion product, i.e., the insert fragment 3 (13349 bp) was recovered by electrophoresis using 1% agarose gel. The complex pCAGGS-MAb01 light chain-IRES-AscI and pCAGGS-MAb02 light chain-IRES-AscI were separately double-digested with Sal I and Asc I, and the insert fragment 3 (4179 bp) was recovered by electrophoresis. Then the linearized vector 3 and the insert fragment 3 were ligated into pinsulator4X-CAG-MAb01-dhfr expression vector and pinsulator4X-CAG-MAb02-dhfr expression vector, both of which were transformed into the E. coli competent DH5a, and the single colonies were screened with ampicillin. At 37° C. and 180 rpm, the single colonies were cultured overnight, the bacterial cells were collected, and the plasmids were extracted, identified through enzyme digestion and subjected to sequence analysis. The results for 1% agarose gel electrophoresis of the Swa I expression vectors pinsulator4X-CAG-MAb01-dhfr and pinsulator4X-CAG-MAb02-dhfr are shown in FIG. 1. The electrophoresis results were shown to be consistent with the theoretical values (2890 bp, 14638 bp).

The sequencing results of the obtained vector showed that the genes of heavy chain and the light chain of the vectors pinsulator4X-CAG-MAb01-dhfr and the pinsulator4X-CAG-MAb02-dhfr were completely consistent with the genetically synthesized sequences.

Example 3

1. Expression of Humanized Anti-Tissue Factor Antibody

CHO-dhfr-cells were seeded into a 6-well plate at a density of $6 \times 10^5$ and cultured overnight. Preparation of transfection complex: 25 μl of Opti-MEM and 4 μl Lipofectamine3000 were added to tube A, shaken at room temperature for 1-2 s, and 25 μl of OptiMEM and 2 μg of plasmid (pinsulator4X-CAG-MAb01-dhfr, pinsulator4X-CAG-MAb02-dhfr) were added to tube B. The mixtures in the above two tubes were mixed, allowed to stand for 5 minutes, and then the resulting mixture was added to the 6-well culture plate. After 24 hours, cells were digested with trypsin and then transferred in a culture plate, and methotrexate (MTX) with a final concentration of 50 μm was added for stress selection. After 20 days, single cell clusters were picked and cultured in 6-well plates. When the confluence of cells reached 90%, the cells were transferred to a T25 culture flask for growth. When the cell density reached $5 \times 10^5$ cells per milliliter, the cells were transferred into an Erlenmeyer flask, vibrated under the conditions of 37° C., 5% $CO_2$, and 130 rpm. After cultured for 15 days, the cell supernatant was collected.

2. Purification of Humanized Anti-Tissue Factor Antibody

Pretreatment of cell culture solution: the cell supernatant was collected and the pH value was adjusted to 9.0, then the cell culture solution was centrifuged at 4° C. and 10,000 rpm for 20 min. The centrifuged mixture was filtered through a 0.22-μm membrane.

Figure 2:
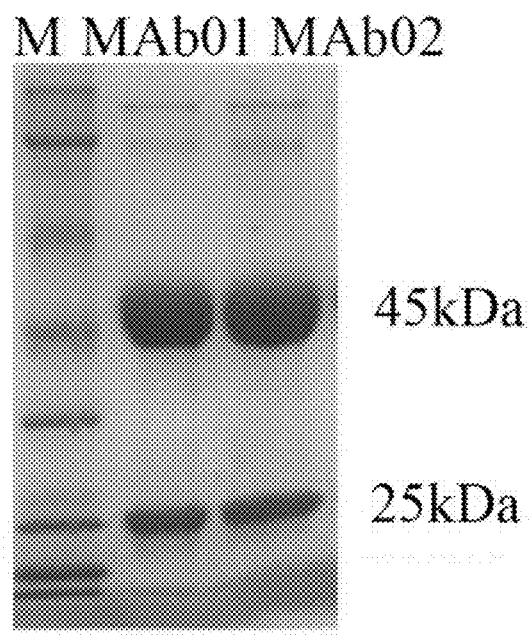
FIG. 2 shows the results for recombinant expression of the heavy chain and the light chain of two humanized anti-tissue factor antibodies.

Purification of Mabselet protein A: the column A was equilibrated with 5 column volumes of equilibrium solution (20 mM Tris HCl 0.15 M NaCl pH 9.0), the cell supernatant was passed through column A at a flow rate of 2 ml/min, and the peak absorption was recorded. After sample loading was completed, washing out and refilling with 5 column volumes of equilibrium solution to the baseline were performed. The target protein was eluted with 100 mM of pH3.0 glycine hydrochloric acid eluent, the fractions at the elution peaks were collected, and then the column A was washed with the equilibrium solution. The collected solution was adjusted to pH 7.0 with 1 M Tris. The target protein was subjected to sodium dodecyl sulfate-polyacrylamide gel electrophoresis (SDS-PAGE) electrophoresis, and the analysis results are shown in FIG. 2.

Analysis of purification results: After the cell fluid with impurity bands was purified by protein A column and gel chromatography, a homogeneous protein was obtained. Based on deduction of the antibody molecular weight and the SDS-PAGE results, it was shown that the 50 KD position was the band for the heavy chain of the humanized anti-tissue factor antibody, and the 25 KD position was the band for the light chain of the humanized anti-tissue factor antibody.

Example 4

Affinity Kinetic Analysis Between Humanized Anti-Tissue Factor Antibody and the Antigen Tissue Factor The humanized anti-tissue factor antibody was coupled to the 2nd channel on the surface of the CM5 chip via amino groups, the 1st and the 3rd channels were used as reference channels, the tissue factor flew through the chip surface as the analyte (mobile phase). The tissue factor mother liquor was diluted to 18 nM, 9 nM, 4.5 nM, 2.25 nM, 1.125 nM as injection concentrations, injected for 120 s, and dissociated for 600 s, and the CM5 chip was regenerated for 30 s using glycine hydrochloric acid (pH 2.0). The Kinetics/Affinity program of Bicore S200 was run to measure the affinity. The affinity of the humanized antibody before modified by the instant applicant was measured to be $3.371 \times 10^{-8}$. The measurement method was consistent with the method used in this experiment, in which the mother liquor was diluted to 12.5 nM, 25 nM, 50 nM, 100 nM and 200 nM, respectively, and the detection results are shown in FIG. 3A-FIG. 3C.

Figure 3A:
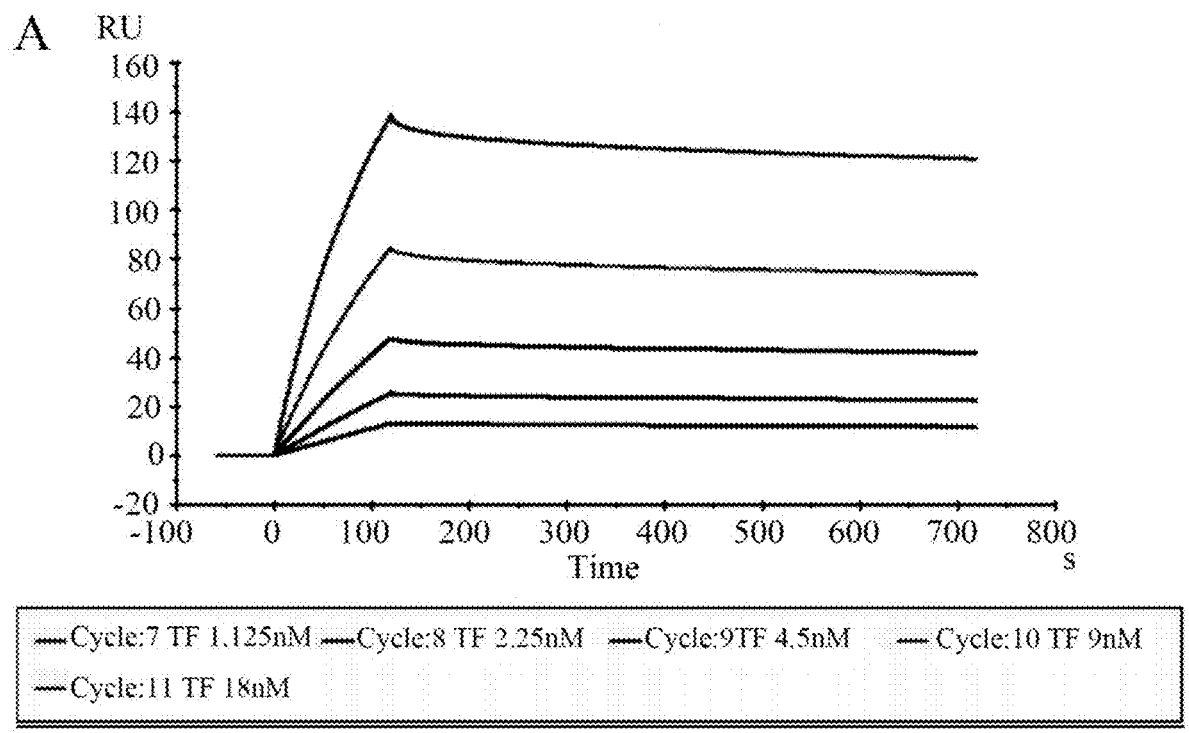
FIG. 3A-FIG. 3C show the results for testing of the affinity between the humanized anti-tissue factor antibody-ADC drug and the tissue, where A is the result for the ADC drug containing the humanized anti-tissue factor antibody MAb01 (MAb01-ADC); and B is the result for the ADC drug containing the humanized anti-tissue factor antibody MAb02 (MAb02-ADC).
Figure 3B:
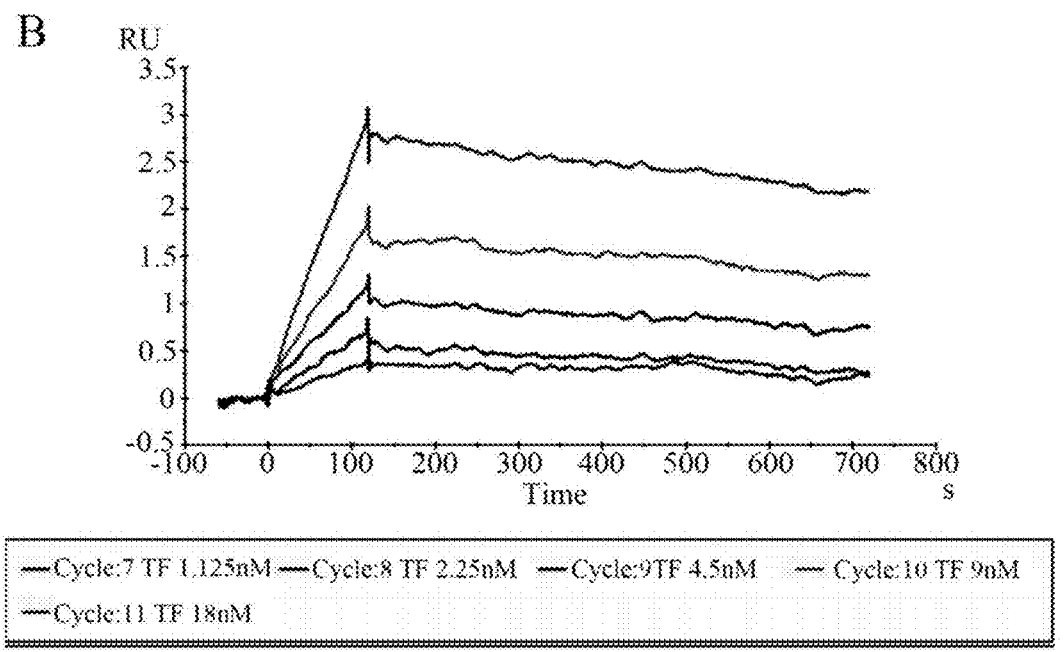
Figure 3C:
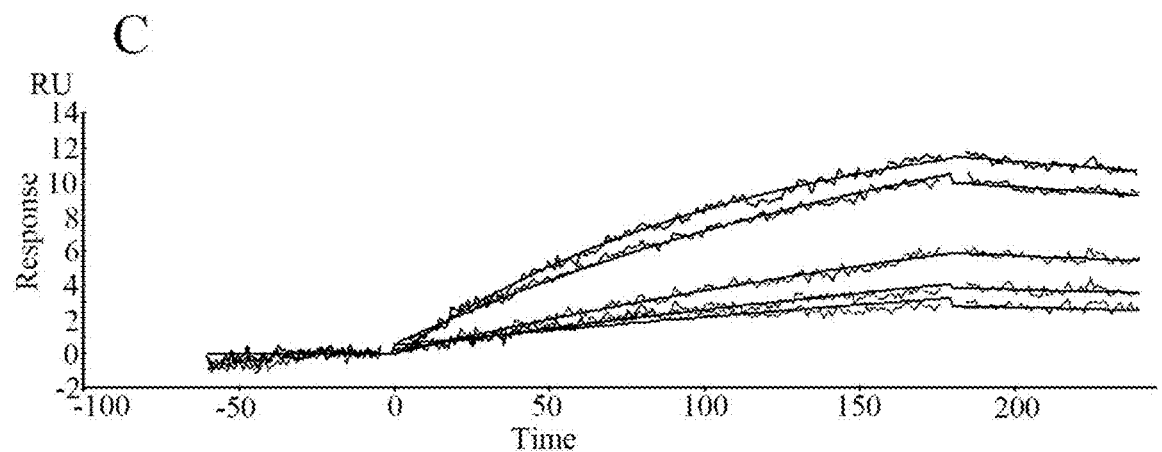

The results are shown in FIG. 3A-FIG. 3C. The association constant (KD) between the humanized anti-tissue factor antibody MAb01 and the tissue factor was $3.57 \times 10^{-10}$ M, and the association constant KD of the humanized anti-tissue factor antibody MAb02 and the tissue factor was $1.002 \times 10^{-9}$ M. All these association constants were higher than those of the antibodies before modified in the previous patent of the instant applicant. Humanized anti-tissue factor antibody MAb01 had the strongest affinity to antigen tissue factor.

Example 5

Detection Method for Expression of Tissue Factor on Surface of Tumor Cells
Expression and Purification of Single-Chain Anti-Tissue-Factor Antibody-GFP Fusion Protein (Tf-Scfv-Gfp)

Figure 4:
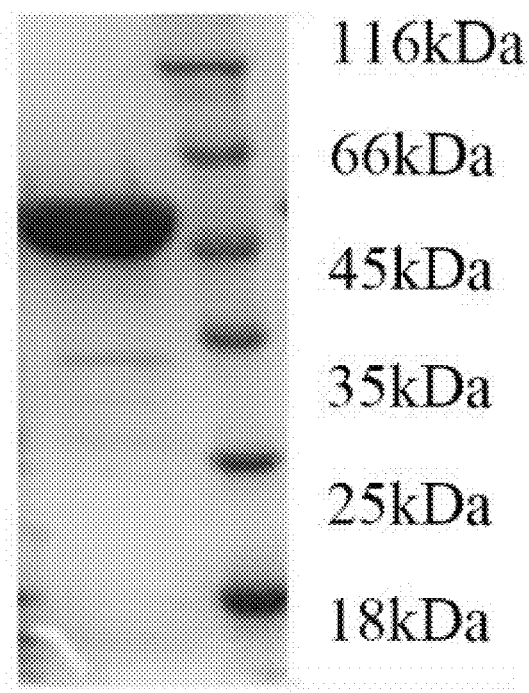
FIG. 4 shows the purification result for the fusion protein of single-chain anti-tissue-factor antibody-GFP.

The heavy chain variable region and light chain variable region of the humanized anti-tissue factor antibody MAb01 (scFv) were fused with green fluorescence Protein (GFP) expressed to obtain a single-chain anti-tissue-factor antibody-GFP fusion protein (the amino acid sequence is SEQ ID NO: 5, QIQLVQSGPELVKPGASVQVSCKTSGYSFT-DYNVYWVRQSPAKGIEWIGYIDPYNGL TIYEQN-FRGKGTLSLDHSTSTAYMELNSLRYEDTAVYF CARDVTTALDFWGQGTSVTVSSGG GGSGGGGS GGGGSDIQMTQSPASISASIGERVTITCLASQT IDTWLAWFLQKPGRSPNLLIYA ATNLADGVPYRFS ASGSGNDFSLTISSLNPEDVATYYCQQVYSSPFTF GQGNKLEIRGGAGG GMSKGEELFTGVVPILVELDG DVNGHKFSVSGEGEGDATYGKLTLKFICTTGKLPV PWPTLV TTFSYGVQCFSRY PDHMKQHDFFKSAMP-EGYVQERTIFFKDDGNYKTRAEVKFEGDTLVNR IELKGIDFKEDGNILGHKLEYNYNSHNVYIMAD-KQKNGIKVNFKIRHNIEDGSVQLADHYQ QNT-PIGDGPVLLPDNHYLSTQSALSKDPNEKRDHM VLLEFVTAAGITHGMDELYK). The gene encoding the single-chain anti-tissue-factor antibody-GFP fusion protein (SEQ ID NO: 6) was cloned into the NcoI/XhoI multiple cloning sites of the expression vector pET-28a (SEQ ID NO: 6, CAAATCCAGCTGGTTCAGAGCGGTCCAGA ACTGGTTAAACCGGGCGCTTCTGTAC AGGTTTCT TGCAAAACCTCCGGTTACTCCTTCACCGACTA-CAATGTGTACTGGGTTCGCC AGTCTCCTGCTA AAGGCATCGAGTGGATCGGTTACATCGACCCGTA-CAACGGCCTGACTA TTTACGAACAGAATTTTCG TGG CAAAGGCACCCTGTCTCTGGATCATTCTACCA GCACCG CTTATATGGAACTGAATAGCCTGCGT-TACGAAGATACCGCGGTTTATTTCTGTGCTCGTGA TGTAACTACTGCCCTGGACTTTTGGGGCCAG GGTACGTCTGTAACCGTAAGCTCTGGTGG TGGCGGTTCTGGCGGTGGTGGTTCTGGT-GGTGGTGGTAGCGATATCCAGATGACCCAGTC TCCGGCTTCCATTAGCGCCTCCATCGGTGAG CGTGTCACCATCACTTGCCTGGCCAGCCA GAC-CATC GATACTTGGCTGGCATGGTTCCTGCAGA AACC GGGTCGTAGCCCAAATCTGCT GATC-TACGCTGCAACGAACCTGGCGGACGGCGTTCCGT-ACCGTTTTCCGCGTCCGGCTC CGGTAA CGACTTCAGCCTGACCATCTCTTCTCTGAACCCT-GAAGATGTCGCAACGTACTA CTGCCAGCAGGTATA-CAGCAGCCCGTTCACCTTCGGTCAGGGCAAC AAACTGGAGATCC GCGGTGGCGCCGGTGGC GGTATGTCTAAAGGTGAAGAGCTGTTTACTGG TGTTGTTCCG ATCCTGGTGGAGCTGGACGGT-GATGTTAACGGCCATAAATTCAGCGTGTCTGGT-GAAGGC GAGGGTGACGCCACCTACGGTAAACTG ACCCTGAAATTCATCTGTACCACGGGCAAACT GCCGGTACCATGGCCGACGCTGGTTACCACCTT CTCCTATGGTGTGCAGTGCTTTTCCCG CTACCC GGACCATATGAAACAGCACGATTTCTTTAAAAGC GCGATGCCGGAAGGCTACGT ACAGGAACGCAC-TATCTTTTTCAAGGACGACGGCAACTATAAAAC CCGTGCAGAAGTCA AATTCGAGGGTGACACC CTGGTCAACCGCATCGAACTGAAAGGCATCGACTT-CAAAGAG GACGGTAACATCCTGGGTCACAAACTG-GAATACAACTATAACTCCCACAACGTGTACATT ATGGCGGATAAGCAGAAAAACGGCATTAAAGT-CAACTTCAAAATCCGCCATAACATTGA AGATGG TTCCGTTCAGCTGGCCGACCACTACCAGCAG AATACTCCGATCGGTGATGGCCC GGTCCTGCT GCCGGATAACCACTACCTGAGCACCCAATCTG TCTGTCCAAGGACCCGA ACGAGAAACGCGAC-CATATGGTTCTGCTGGAATTTGTAACCGCGGCGG GTATCACTCACG GCATGGATGAACTGTATAAA). After the recombinant vector was successfully constructed, it was transformed into the competent cells of expression strain BL21 (DE3). The cells were cultivated overnight at 37° C., and inoculated into a new culture medium the next day. When OD 600 is 0.6, IPTG was added to a final concentration of 1 mM, and the resulting mixture was induced overnight at a low temperature of 16° C. The culture mixture was centrifuged and the bacterial cells were collected. The bacterial cells were subjected to sonication and Ni-column affinity chromatography to obtain a TF-scFv-GFP fusion protein with a protein molecular weight of about 57 kDa. The purification result of TF-scFv-GFP is shown in FIG. 4.

Detection of Tissue Factor Proteins on Cell Surface Using Single-Chain Anti-Tissue-Factor Antibody-GFP Fusion Protein A 96-well ELISA black detection plate was coated with tissue factor protein (purchased from Taiyuan Bo-Ao-Te Biotech, Co., Ltd., catalogue number: BAT1001) at a concentrations of 300 pmol, 150 pmol, 75 pmol, 37.5 pmol, 18.75 pmol, and 9.375 pmol of tissue factor protein, respectively. A certain amount of tumor cells (SK-OV-3/BXPC-3 cell strain, about $1\times10^6$ cells; Hela cell strain, about $1\times10^7$ cells; and A549/SW620 cell strain, about $1\times10^8$ cells) were immobilized in a 96-well cell culture plate and single-chain anti-tissue-factor antibody-GFP fusion protein and positive control antibody (Abcam FITC fluorescent Anti-Tissue Factor antibody (ab275690) were added, respectively. After 1 hour of incubation, the culture solution was washed with PBS (pH 7.3) 1-2 times, PBS buffer was added to resuspend, and the resulting solution was detected on-board at an excitation wavelength of 493 nm and an emission wavelength of 528 nm.

Figure 5A:
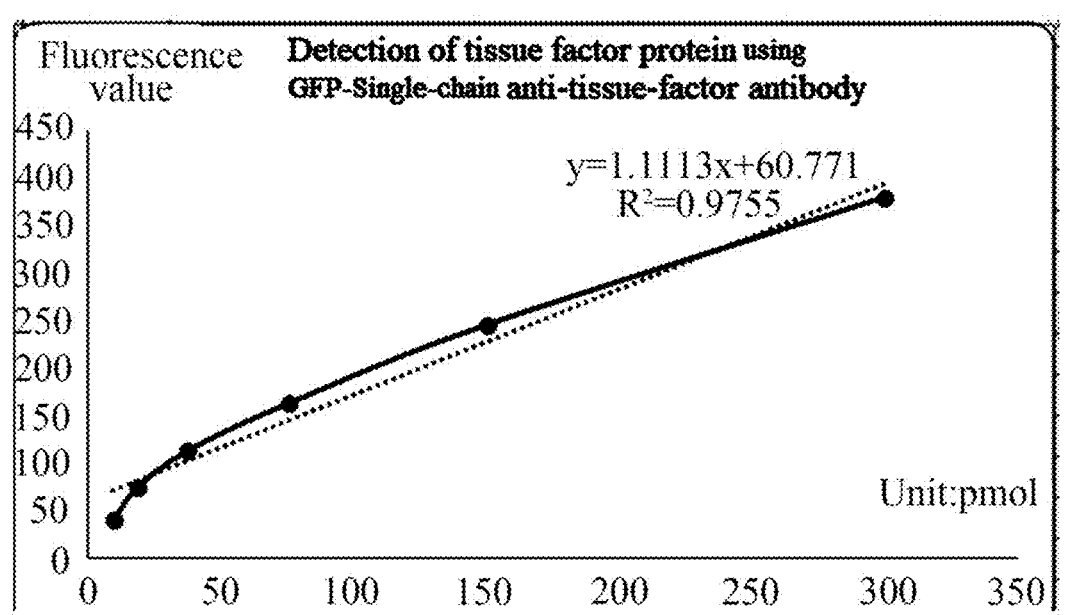
FIG. 5A-FIG. 5B show a standard curve of the tissue factor protein, where A is a standard curve for detection of tissue factor protein using GFP-tissue factor single-chain antibody, and B is a standard curve for detection of tissue factor protein using FITC-tissue factor antibody.
Figure 5B:
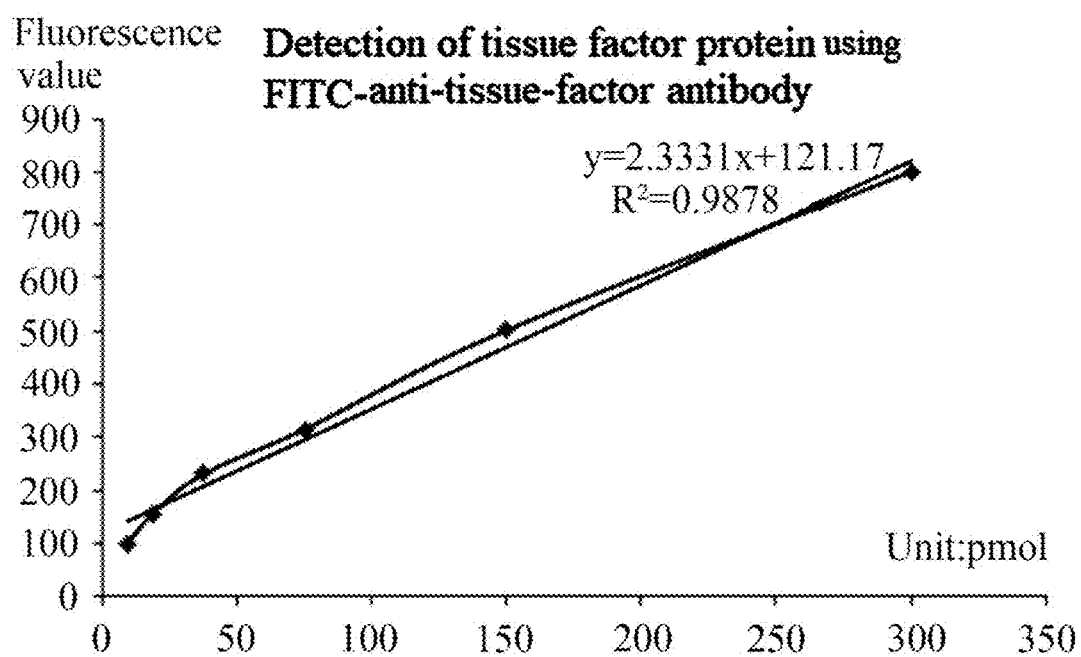
Figure 6A:
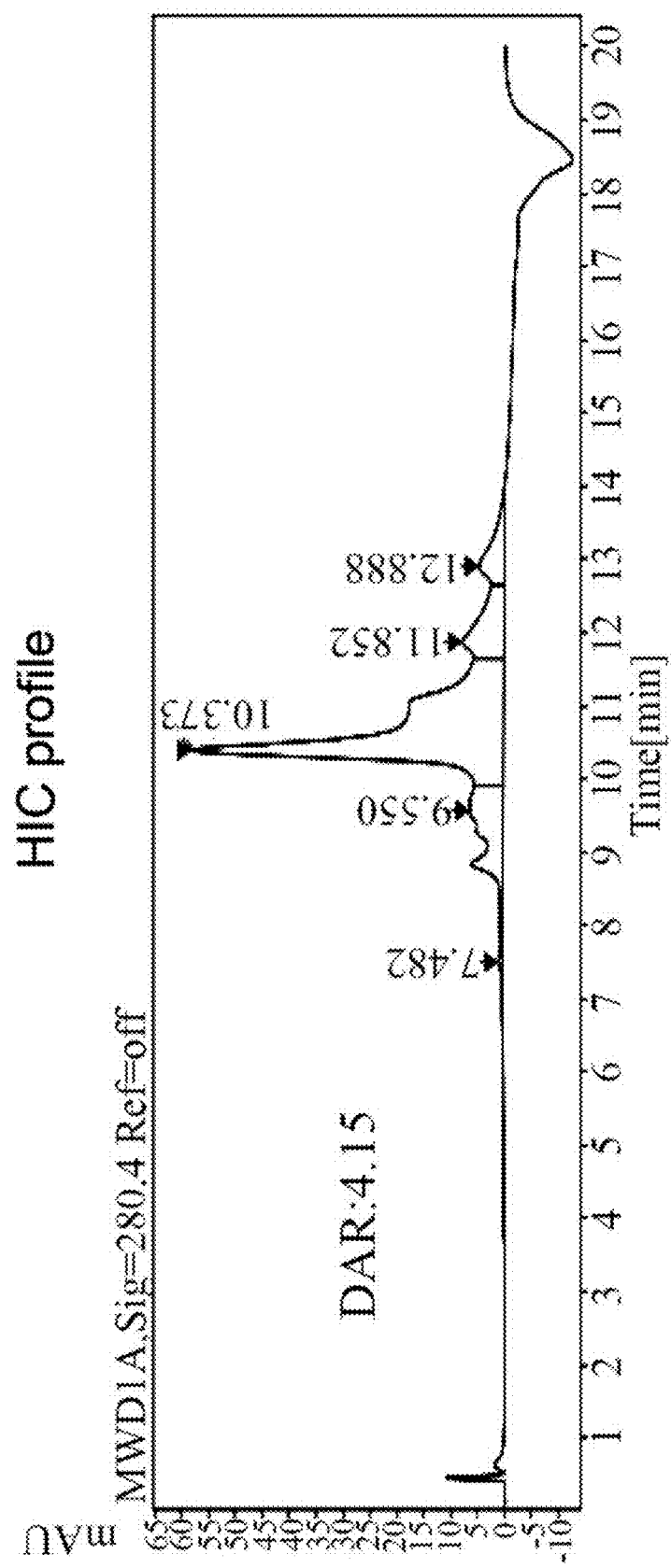
FIG. 6A-FIG. 6B show the coupling result for MAb01-ADC.
Figure 6B:
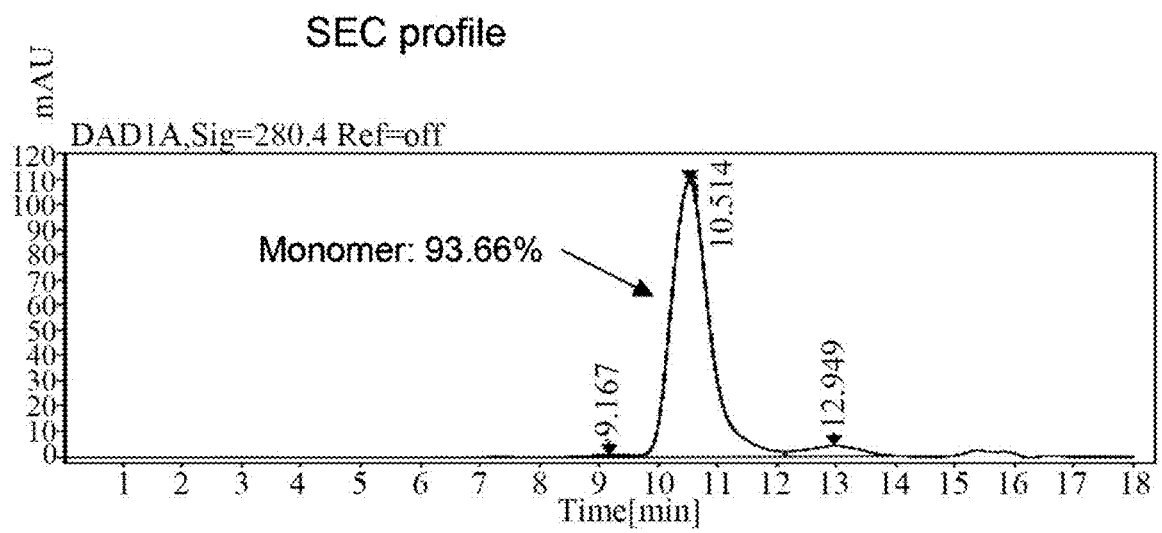
Figure 7A:
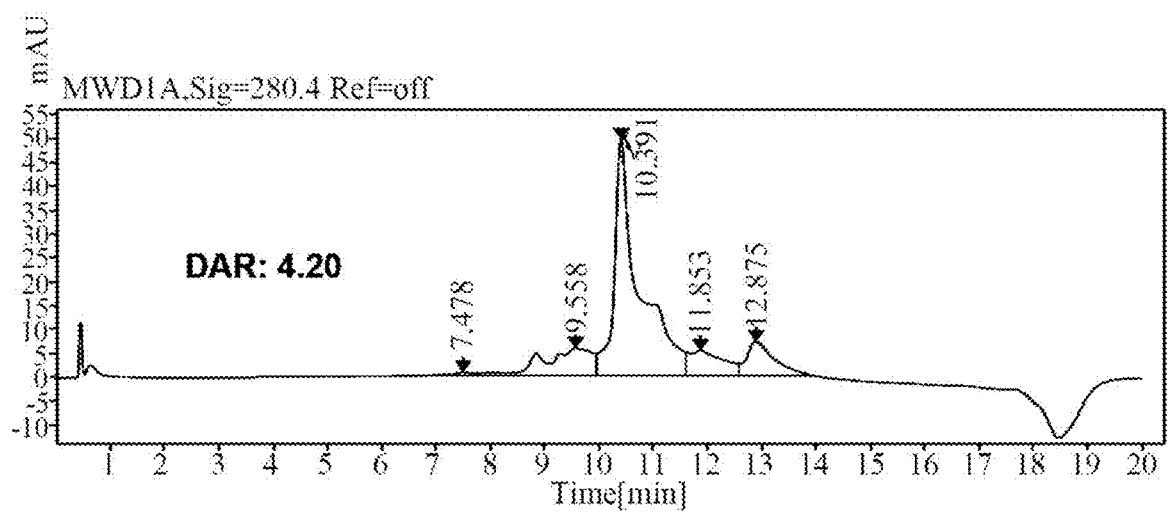
FIG. 7A-FIG. 7B show the coupling result for MAb02-ADC.
Figure 7B:
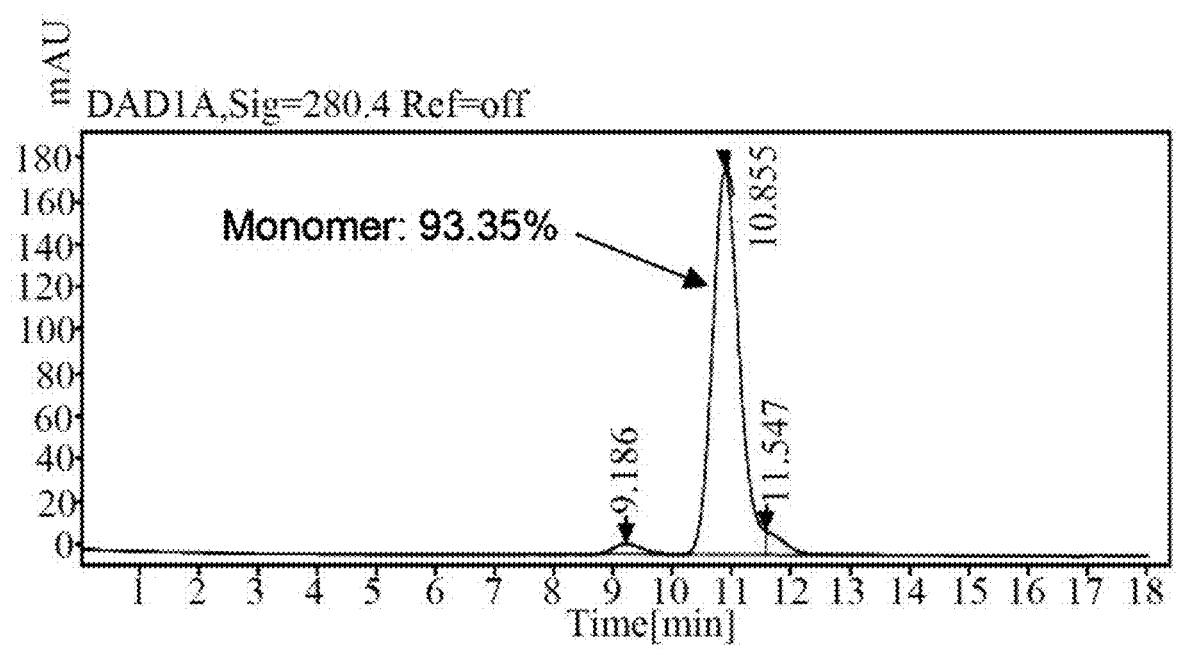
Figure 8A:
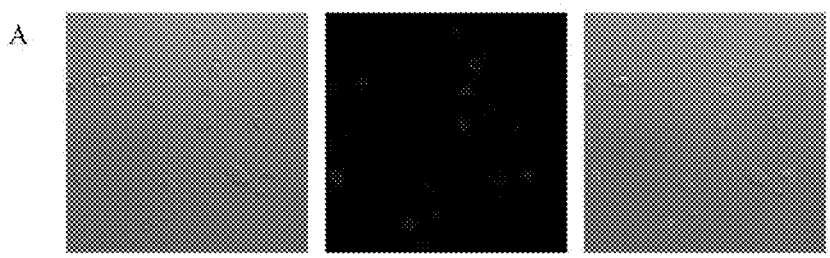
FIG. 8A-FIG. 8E are the results for endocytosis of humanized anti-tissue factor antibody MAb-ADC drug in tumor cells, where A is the result for endocytosis of MAb02-ADC in SK-OV-3 cells; B is the result for endocytosis result of MAb02-ADC in BXPC cells; C is the result for endocytosis of MAb01-ADC in SK-OV-3 cells; D is the result for endocytosis result of MAb01-ADC in BXPC cells; and E is the result for endocytosis result of MAb01-ADC in A549 cells.
Figure 8B:
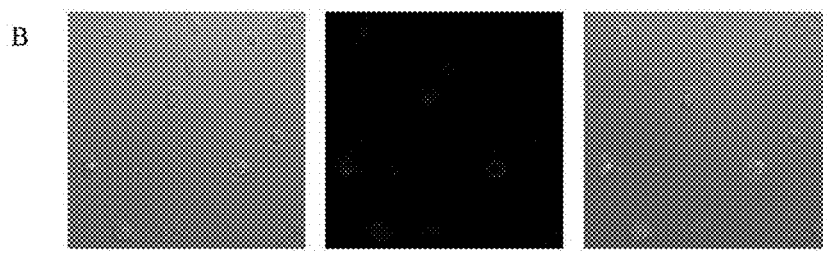
Figure 8C:
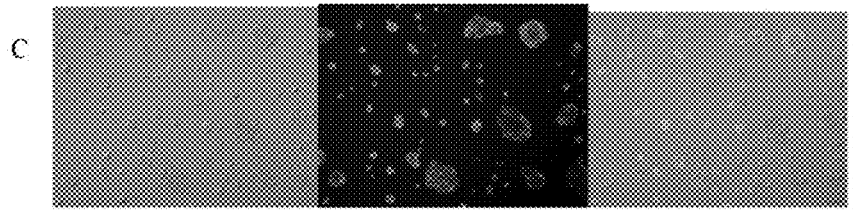
Figure 8D:
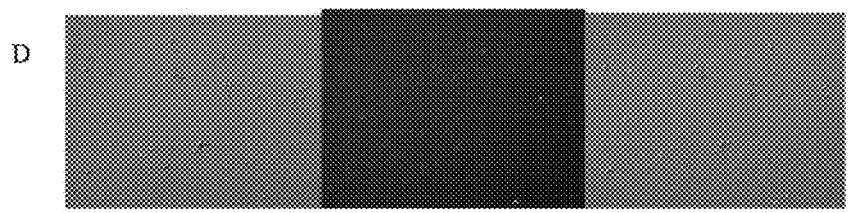
Figure 8E:
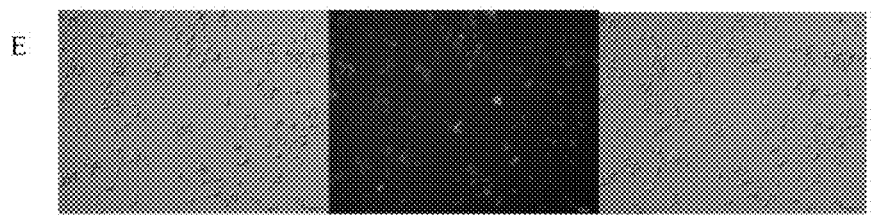

The prepared standard curves are shown in FIG. 5A-FIG. 5B.

The expression amount of the tissue factor on the surface of tumor cells was measured according to the above method. The results are shown in Table 3. The results of detecting tissue factor protein on cell surface using the single-chain anti-tissue-factor antibody-GFP fusion protein were consistent with the detection results for the positive-control antibody, indicating that the detection method is feasible in this example. The results showed that SK-OV-3 and BXPC-3 cell strains had the highest expression levels of tissue factor on the surface, while the SW620 and A549 cell strains had the lowest expression levels of tissue factor on the surface. According to the fact that there are $6.02\times10^{23}$ molecules in 1 mol, the number of targets for the tissue factor on the surface of each type of tumor cells was calculated, as is shown in Table 4.

TABLE 3

Expression amount of tissue factor on the surface of tumor cells

| Cell name | Tissue factor on cell surface (single-chain anti-tissue-factor antibody-GFP) | Tissue factor on cell surface (positive antibody) | Number of cells |
| --- | --- | --- | --- |
| SK-OV-3 cell strain | 136 pmol | 141 pmol | $10^6$ |
| BXPC-3 cell strain | 119 pmol | 125 pmol | $10^6$ |
| hela cell strain | 56 pmol | 67.6 pmol | $10^7$ |
| SW620 cell strain | 32.6 pmol | 37.2 pmol | $10^8$ |
| A549 cell strain | 22.7 pmol | 28.2 pmol | $10^8$ |

TABLE 4

Number of target on surface of tumor cells

| Cell name | Target number/cell |
| --- | --- |
| SK-OV-3 cell strain | $8.18 \times 10^7$ |
| BXPC-3 cell strain | $7.16 \times 10^7$ |
| hela cell strain | $3.37 \times 10^6$ |
| SW620 cell strain | $3.26 \times 10^4$ |
| A549 cell strain | $1.36 \times 10^4$ |

Example 6

Experiment on Coupling of ADC Drug Containing Humanized Anti-Tissue Factor Antibody The antibody (5 mg/mL) was added in a coupling buffer (20 mM His-His. HCl, pH=5.96), and the coupling was carried out directly. The antibody, DTPA (diethylenetriaminepentaacetic acid, 10 mM) and TCEP (tris(2-carboxyethyl) phosphine hydrochloride, 10 mM) were added sequentially according to Table 5. Upon completion of addition of each component, the resulting mixture was vortexed briefly to mix thoroughly. Finally, the resulting mixture was centrifuged briefly to settle the reaction system at the bottom of the tube, then the tube was placed in a constant-temperature mixer, and a reduction reaction was carried out according to the conditions shown in Table 5. After the reduction reaction was completed, a corresponding amount of DMSO (dimethyl sulfoxide) was added in the respective reaction system and vortexed briefly to mix thoroughly. Then a corresponding amount of Linker-payload (5 mM) was added and vortexed briefly to mix thoroughly and then centrifuged. The reaction system was settled to the bottom of the tube, the reaction system was placed in a constant-temperature mixer, and the coupling reaction was carried out according to the conditions shown in Table 6. After completion of the coupling reaction, an amount of ADC was sampled using an HIC-HPLC method (see Table 7). The ADC was repeatedly dialyzed in an ultrafiltration centrifuge tube (30 KDa) for several times, and an appropriate amount of ADC for concentration measurement, HIC-HPLC, SEC-HPLC, and free drug residue measurement.

TABLE 5

Parameters for reduction reaction

| Antibody | Linker-payload | Equivalent (Eq) ratio of each component Antibody | TCEP | DTPA Final concentration | Reduction condition |
| --- | --- | --- | --- | --- | --- |
| MAb01 | Mc-VC-PAB-MMAE | 1 | 3 | 1 mM | 25° C., 400 rpm, 1.5 h |
| MAb02 | Mc-VC-PAB-MMAE | 1 | 3 | 1 mM | 25° C., 400 rpm, 1.5 h |

TABLE 6

Parameters for coupling reaction

| Antibody | Linker-payload | Equivalent (Eq) ratio of each component Antibody | Linker-payload | DMSO ratio | Coupling conditions |
| --- | --- | --- | --- | --- | --- |
| MAb01 | Mc-VC-PAB-MMAE | 1 | 7 | 20% | 25° C., 400 rpm, 1.5 h |

TABLE 6-continued

Parameters for coupling reaction

| Antibody | Linker-payload | Equivalent (Eq) ratio of each component | | DMSO ratio | Coupling conditions |
|---|---|---|---|---|---|
| | | Antibody | Linker-payload | | |
| MAb02 | Mc-VC-PAB-MMAE | 1 | 7 | 20% | 25° C., 400 rpm, 1.5 h |

TABLE 7

Experiment results for DAR reduction-coupling

| Sample number | Concentration (UV mg/mL) | Purity (SEC-HPLC, %) | DAR(HIC-HPLC) |
|---|---|---|---|
| MAb01 | 4.16 | 93.66% | 4.15 |
| MAb02 | 4.09 | 92.35% | 4.20 |

Example 7

Cell Endocytosis Experiment of ADC Drug Containing Humanized Anti-Tissue Factor Antibody MAb01

Tumor cells with high- and low-expression of tissue factor were cultured and digested with trypsin when the confluence reached 90%, 250,000 cells were spread on a confocal dish, cultured, and allowed to adhere to the wall. After adhering, the original culture medium was removed and 1 ml of culture medium containing 1 μl of fluorescently labeled (e.g., with FITC) MAb01-ADC drug or MAb02-ADC was added. Starting from the addition of the antibody, the cells were observed under a confocal microscope (Zeiss LSM 710, 20 times of magnification). The timing was set at min 0, and the field of view having a uniform density and single cells was selected. The time was set to 20 minutes for a cycle. After 6-8 cycles, pictures were taken.

The experimental results are shown in FIG. 8A-FIG. 8E. The antibody MAb01-ADC drug started to be endocytized in half an hour and endocytosis was completed within 2 hours. Both SK-OV-3 cell strain and A549 cell strain allows for endocytosis. The antibody MAb02-ADC-ADC drug showed a longer endocytosis time and can be endocytized by SK-OV-3 cell strain but not endocytized by A549 cell strain. It can be seen that the ADC drugs containing the humanized anti-tissue factor antibody with high affinity can be endocytized in tumor cells with low-expression tissue factor.

Example 8

Detection of Biological Activity of High Affinity Humanized Anti-Tissue Factor Antibody-ADC The cell lines used in this example were purchased from the Cell Bank of the Chinese Academy of Sciences and cultured according to the corresponding instructions, including SK-vo-3 (human ovarian cancer cell strain), A549 (human non-small cell lung cancer), BXPC (pancreatic cancer cell strain), SW620 (colon cancer cell strain), Hela cell strain (cervical cancer cell strain), and the drug IgG-MMAE was used as control. Cells in the logarithmic growth phase were seeded into a 96-well cell culture plate at a density of 5,000 cells per well, with 100 microliters of cells added in each well. After the cells were incubated for about 16 hours at 37° C. and 5% carbon dioxide, different concentrations of the antibody MAb01-ADC drug were added, with 3 duplicate wells set for each drug concentration. After 3 days of treatment, the culture medium was discarded. CCK-8 reaction solution was added, with 100 microliters for each well. The resulting mixture was reacted at 37° C. to an expected color depth, the cell viability of each group (OD 450) was measured, and the cell survival rate was calculated according to the following Equation I. For cell strains (SK-vo-3 (human ovarian cancer cell strain), BXPC (pancreatic cancer cell strain), and Hela cell strain (cervical cancer cell strain)) that enable endocytosis, relevant experiments had also been conducted with MAb02-ADC drug.

$$\text{Survival rate (\%)} = (OD \text{ administration} - OD blank)/(OD \text{ control} - OD \text{ blank}) \times 100\%$$

Equation I

The above data were analyzed by GraphPad Prism 5 software, and the $IC_{50}$ values of TF-ADC on different cell strains were calculated.

Figure 9A:
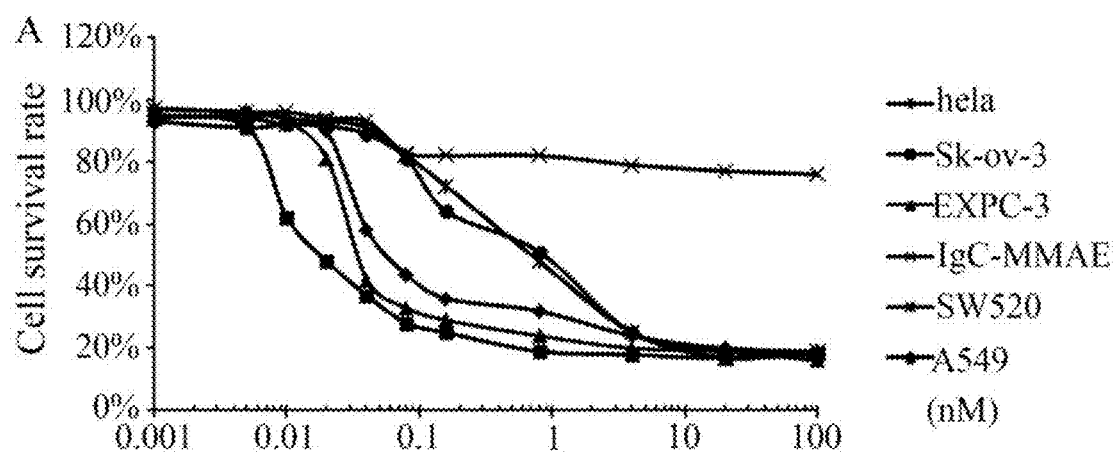
FIG. 9A-FIG. 9B show the results of inhibitory effect of the MAb01-ADC on different types of tumor cells; where A is the inhibitory effect of MAb01-ADC on tumor cells; and B is the inhibitory effect of MAb02-ADC on tumor cells.
Figure 9B:
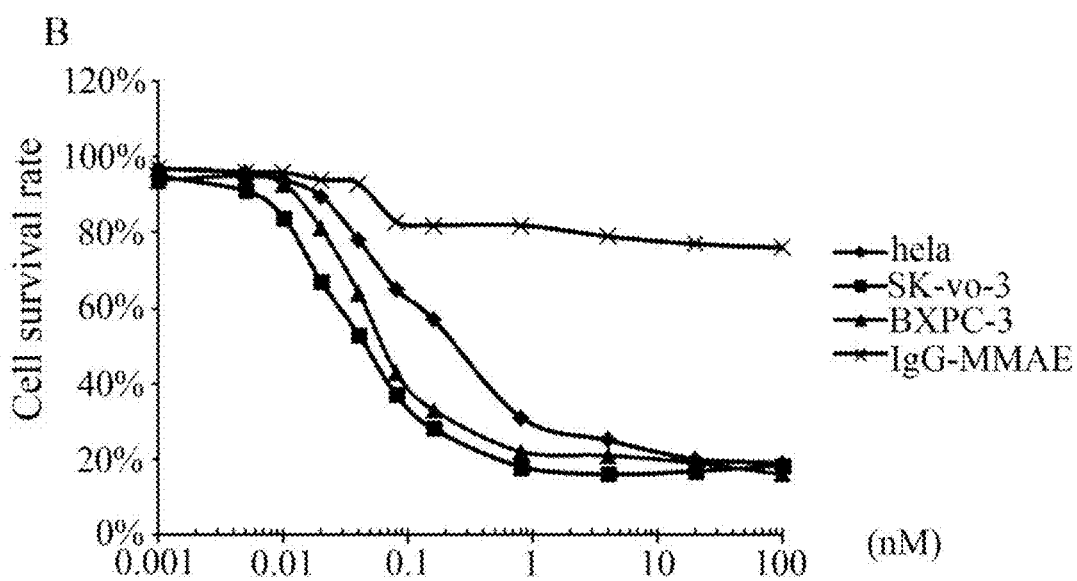

The results are shown in FIG. 9A-FIG. 9B. The antibody MAb01-ADC drugs could better inhibit the growth of tumor cells with high expression in tissues in vitro, and its inhibitory effect was proportional to the number of tissue factor molecules on the cell surface. The MAb02-ADC drugs also had an inhibitory effect on the tumor cells that enable endocytosis.

The $IC_{50}$ values of the MAb01-ADC drugs against different types of cancer cells are shown in Table 8.

TABLE 8

$IC_{50}$ values of MAb01-ADC drug against different types of cancer cells
$IC_{50}$ (antibody MAb01-ADC drug) (nM)

| Cervical Cancer Cell Hela | 0.0436 |
|---|---|
| Ovarian cancer cell SK-OV-3 | 0.0136 |
| In-situ adenocarcinoma cells BXPC | 0.0308 |
| Colon cancer cell SW620 | 0.4632 |
| Non-small cell lung cancer A549 | 0.4513 |

Example 9

Experiment of ADC Drug Containing Humanized Anti-Tissue Factor Antibody to Inhibit Mouse Subcutaneous Tumor A nude mouse subcutaneous tumor model was used for the selection of tumor cells. In every 100 nude mice, one strain of tumor cells was implanted. When the tumor volume reached 64-100 cubic millimeters, 6 experimental groups were determined, with 8 mice in each group, and the antibody MAb01-ADC drugs were used to treat the tumors at a dose of 1 mg/kg, 2 mg/kg, and 4 mg/kg, respectively. 2 mg/kg of ADC was used in combination with gemcitabine 50 mg/kg, with gemcitabine used as the positive control at a dosage of 50 mg/kg, and PBS as the negative control. Tail vein administration began on Day 0. The body weight of the nude mice was measured every other day and the tumor length and diameter data were measured with a vernier caliper. At the end of the experiment, blood was collected and the serum was stored. The animals were sacrificed by cervical dislocation, and the tumor mass was harvested and weighed. The drug efficacy was evaluated based on change in tumor weight and in relative volume.

Tumor volumes were calculated according to Equation II.

$$V = a \times b \times c \quad \text{Equation II}$$

Where, a, b, and c represent the length, width, and height of the tumor, respectively.

Figure 10A:
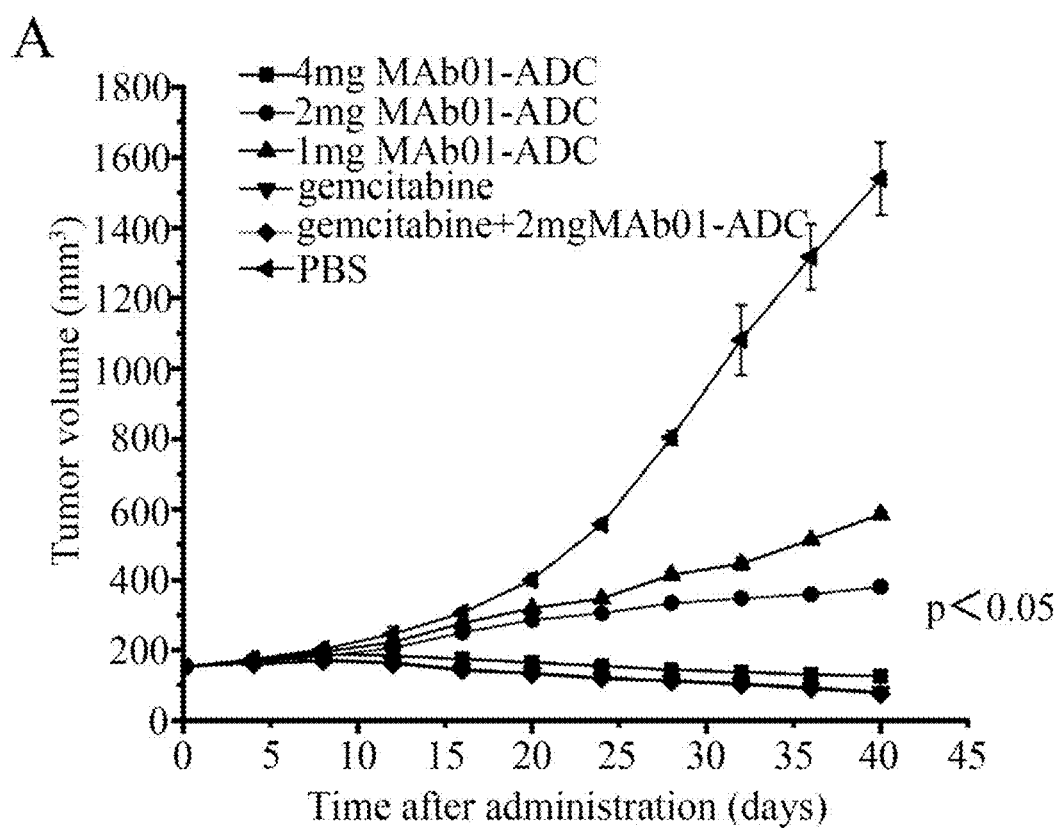
FIG. 10A-FIG. 10B show the inhibitory effect of MAb01-ADC on tumor-bearing growth in nude mice in a subcutaneous tumor model, where A is for BXPC cells and B is for SK-OV-3 cells.
Figure 10B:
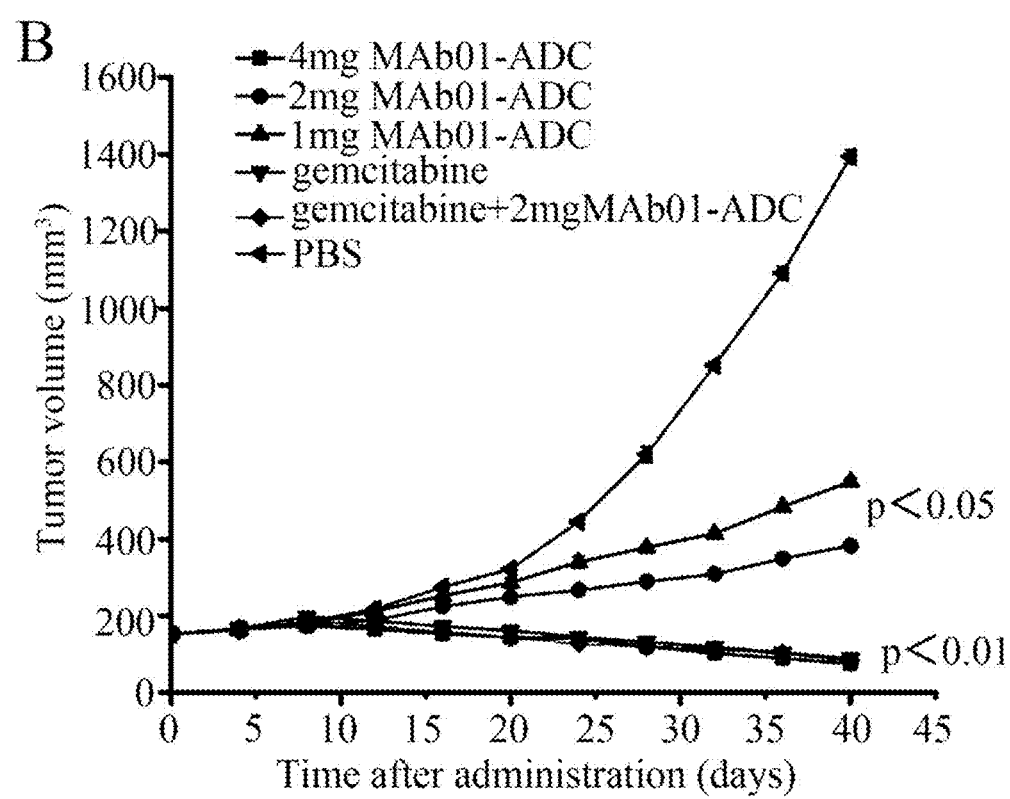

As shown in FIG. 10A-FIG. 10B, the MAb01-ADC drug could significantly inhibit the growth of ovarian cancer and pancreatic cancer tumors in a dose-dependent manner.

Described above are only preferred embodiments of the present disclosure. It should be pointed out that those of ordinary skill in the art can make several improvements and modifications without departing from the principles of the present disclosure. These improvements and modifications should also be regarded as falling within the protection scope of the present disclosure.

---

SEQUENCE LISTING

```
Sequence total quantity: 49
SEQ ID NO: 1            moltype = AA  length = 449
FEATURE                 Location/Qualifiers
source                  1..449
                        mol_type = protein
                        note = amino acid sequence of heavy chain of humanized
                          anti-tissue factor antibody
                        organism = synthetic construct
SEQUENCE: 1
QIQLVQSGPE VVKPGASVRV SCKGSGYSFT DYNIYWVRQS PAKGLEWIGY IDPYNGLTIY   60
DQNFRAKATL SVDHSTSNAY MEINSLRYED TAVYFCARDV TSALEFWGQG TSVTVSSEFA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 2            moltype = AA  length = 214
FEATURE                 Location/Qualifiers
source                  1..214
                        mol_type = protein
                        note = amino acid sequence of light chain of humanized
                          anti-tissue factor antibody
                        organism = synthetic construct
SEQUENCE: 2
DIQMTQSPAS ISASVGERVT ITCLGSQTID TYLAWYLQKP GRSPQLLIYA ATQLADGVPS   60
RFSASGSGTD FSLTISSLQP EDVATYYCQN VYSSPFTFGQ GNKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 3            moltype = AA  length = 449
FEATURE                 Location/Qualifiers
source                  1..449
                        mol_type = protein
                        note = amino acid sequence of heavy chain of a humanized
                          anti-tissue factor antibody compared with that of the
                          present invention
                        organism = synthetic construct
SEQUENCE: 3
QIQLVQSGPE LVKPGASVQV SCKTSGYSFT DYNVYWVRQS PAKGIEWIGY IDPYNGLTIY   60
EQNFRGKGTL SLDHSTSTAY MELNSLRYED TAVYFCARDV TTALDFWGQG TSVTVSSEFA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGK                                   449

SEQ ID NO: 4            moltype = AA  length = 214
FEATURE                 Location/Qualifiers
source                  1..214
                        mol_type = protein
                        note = amino acid sequence of light chain of a humanized
                          anti-tissue factor antibody compared with that of the
                          present invention
                        organism = synthetic construct
SEQUENCE: 4
DIQMTQSPAS ISASIGERVT ITCLASQTID TWLAWFLQKP GRSPNLLIYA ATNLADGVPY   60
RFSASGSGND FSLTISSLNP EDVATYYCQQ VYSSPFTFGQ GNKLEIRRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 5            moltype = AA  length = 483
```

```
FEATURE                   Location/Qualifiers
source                    1..483
                          mol_type = protein
                          note = amino acid sequence of the single-chain fusion
                            protein
                          organism = synthetic construct
SEQUENCE: 5
QIQLVQSGPE LVKPGASVQV SCKTSGYSFT DYNVYWVRQS PAKGIEWIGY IDPYNGLTIY    60
EQNFRGKGTL SLDHSTSTAY MELNSLRYED TAVYFCARDV TTALDFWGQG TSVTVSSGGG   120
GSGGGGSGGG GSDIQMTQSP ASISASIGER VTITCLASQT IDTWLAWFLQ KPGRSPNLLI   180
YAATNLADGV PYRFSASGSG NDFSLTISSL NPEDVATYYC QQVYSSPPTF GQGNKLEIRG   240
GAGGGMSKGE ELFTGVVPIL VELDGDVNGH KFSVSGEGEG DATYGKLTLK FICTTGKLPV   300
PWPTLVTTFS YGVQCFSRYP DHMKQHDFFK SAMPEGYVQE RTIFFKDDGN YKTRAEVKFE   360
GDTLVNRIEL KGIDFKEDGN ILGHKLEYNY NSHNVYIMAD KQKNGIKVNF KIRHNIEDGS   420
VQLADHYQQN TPIGDGPVLL PDNHYLSTQS ALSKDPNEKR DHMVLLEFVT AAGITHGMDE   480
LYK                                                                 483

SEQ ID NO: 6              moltype = DNA  length = 1449
FEATURE                   Location/Qualifiers
source                    1..1449
                          mol_type = other DNA
                          note = nucleotide sequence of the gene encoding the
                            single-chain fusion protein
                          organism = synthetic construct
SEQUENCE: 6
caaatccagc tggttcagag cggtccagaa ctggttaaac cgggcgcttc tgtacaggtt    60
tcttgcaaaa cctccggtta ctccttcacc gactacaatg tgtactgggt tcgccagtct   120
cctgctaaag catcgagtg gatcggttac atcgacccgt acaacggcct gactatttac   180
gaacagaatt tcgtggcaa aggcaccctg tctctggatc attctaccag caccgcttat   240
atggaactga atagcctgcg ttacgaagat accgcggttt atttctgtgc tcgtgatgta   300
actactgccc tggactttgg gggccagggt acgtctgtaa ccgtaagctc tggtggtggc   360
ggttctggcg gtggtggttc tggtggtggt ggtagcgata tccagatgac ccagtctccg   420
gcttccatta gcgcctccat cggtgagcgt gtcaccatca cttgcctggc cagccagacc   480
atcgatactt ggctggcatg gttcctgcag aaacgggtc gtagcccaaa tctgctgatc   540
tacgctgcaa cgaacctggc ggacggcgtt ccgtaccgtt tttccgcgtc cggctccggt   600
aacgacttca gcctgaccat ctcttctctg aaccctgaag atgtcgcaac gtactactgc   660
cagcaggtat acagcagccc gttcaccttc ggtcagggca caaaactgga gatccgcggt   720
ggcgccggtg gcggtatgtc taaaggtgaa gagctgtttc tggtgttgt tccgatcctg   780
gtggagctga acggtgatgt taacggccat aaattcagcg tgtctggtga aggcgagggt   840
gacgccacct acggtaaact gaccctgaaa ttcatctgta ccacgggcaa actgccggta   900
ccatggccga cgctggttac cacctttctcc tatggtgtgc agtgctttttc ccgctacccg   960
gaccatatga acagcacga tttctttaaa agcgcgatgc cggaaggcta cgtacaggaa  1020
cgcactatct ttttcaagga cgacggcaac tataaaaccc gtgcagaagt caaattcgaa  1080
ggtgacaccc tggtcaaccg catcgaactg aaaggcatcg acttcaaaga ggacggtaac  1140
atcctgggtc acaaactgga atacaactat aactcccaca cgtgtacat tatggcggat  1200
aagcagaaaa acggcattaa agtcaacttc aaaatccgcc ataacattga agatggttcc  1260
gttcagctgg ccgaccacta ccagcagaat actccgatcg gtgatggccc ggtcctgctg  1320
ccggataacc actacctgag cacccaatct gctctgtcca aggacccgaa cgagaaacgc  1380
gaccatatgg ttctgctgga atttgtaacc gcggcgggta tcactcacgg catggatgaa  1440
ctgtataaa                                                         1449

SEQ ID NO: 7              moltype = AA  length = 30
FEATURE                   Location/Qualifiers
source                    1..30
                          mol_type = protein
                          note = Sequence of heavy chain variable region in the FR1
                            region before modification
                          organism = synthetic construct
SEQUENCE: 7
EVQLQQSGPE LVKPGASVKV SCKASGYTFT                                    30

SEQ ID NO: 8              moltype = AA  length = 30
FEATURE                   Location/Qualifiers
source                    1..30
                          mol_type = protein
                          note = Sequence of heavy chain variable region in the FR1
                            region of the humanized anti-tissue factor antibody MAb01
                          organism = synthetic construct
SEQUENCE: 8
QIQLVQSGPE LVKPGASVQV SCKTSGYSFT                                    30

SEQ ID NO: 9              moltype = AA  length = 30
FEATURE                   Location/Qualifiers
source                    1..30
                          mol_type = protein
                          note = Sequence of heavy chain variable region in the FR1
                            region of the humanized anti-tissue factor antibody MAb02
                          organism = synthetic construct
SEQUENCE: 9
```

```
QIQLVQSGPE VVKPGASVRV SCKGSGYSFT                                          30

SEQ ID NO: 10           moltype = AA  length = 5
FEATURE                 Location/Qualifiers
source                  1..5
                        mol_type = protein
                        note = Sequence of heavy chain variable region in the CDR1
                         region before modification
                        organism = synthetic construct
SEQUENCE: 10
HFNVY                                                                    5

SEQ ID NO: 11           moltype = AA  length = 5
FEATURE                 Location/Qualifiers
source                  1..5
                        mol_type = protein
                        note = Sequence of heavy chain variable region in the CDR1
                         region of the humanized anti-tissue factor antibody MAb01
                        organism = synthetic construct
SEQUENCE: 11
DYNVY                                                                    5

SEQ ID NO: 12           moltype = AA  length = 5
FEATURE                 Location/Qualifiers
source                  1..5
                        mol_type = protein
                        note = Sequence of heavy chain variable region in the CDR1
                         region of the humanized anti-tissue factor antibody MAb02
                        organism = synthetic construct
SEQUENCE: 12
DYNIY                                                                    5

SEQ ID NO: 13           moltype = AA  length = 14
FEATURE                 Location/Qualifiers
source                  1..14
                        mol_type = protein
                        note = Sequence of heavy chain variable region in the FR2
                         region before modification
                        organism = synthetic construct
SEQUENCE: 13
WVRQSPGKGL EWIG                                                          14

SEQ ID NO: 14           moltype = AA  length = 14
FEATURE                 Location/Qualifiers
source                  1..14
                        mol_type = protein
                        note = Sequence of heavy chain variable region in the FR2
                         region of the humanized anti-tissue factor antibody MAb01
                        organism = synthetic construct
SEQUENCE: 14
WVRQSPAKGI EWIG                                                          14

SEQ ID NO: 15           moltype = AA  length = 14
FEATURE                 Location/Qualifiers
source                  1..14
                        mol_type = protein
                        note = Sequence of heavy chain variable region in the FR2
                         region of the humanized anti-tissue factor antibody MAb02
                        organism = synthetic construct
SEQUENCE: 15
WVRQSPAKGL EWIG                                                          14

SEQ ID NO: 16           moltype = AA  length = 16
FEATURE                 Location/Qualifiers
source                  1..16
                        mol_type = protein
                        note = Sequence of heavy chain variable region in the CDR2
                         region before modification
                        organism = synthetic construct
SEQUENCE: 16
YIDPDNGITF YDENFM                                                        16

SEQ ID NO: 17           moltype = AA  length = 16
FEATURE                 Location/Qualifiers
source                  1..16
                        mol_type = protein
                        note = Sequence of heavy chain variable region in the CDR2
                         region of the humanized anti-tissue factor antibody MAb01
                        organism = synthetic construct
```

```
SEQUENCE: 17
YIDPYNGLTI YEQNFR                                                                16

SEQ ID NO: 18           moltype = AA  length = 16
FEATURE                 Location/Qualifiers
source                  1..16
                        mol_type = protein
                        note = Sequence of heavy chain variable region in the CDR2
                         region of the humanized anti-tissue factor antibody MAb02
                        organism = synthetic construct
SEQUENCE: 18
YIDPYNGLTI YDQNFR                                                                16

SEQ ID NO: 19           moltype = AA  length = 33
FEATURE                 Location/Qualifiers
source                  1..33
                        mol_type = protein
                        note = Sequence of heavy chain variable region in the CDR3
                         region before modification
                        organism = synthetic construct
SEQUENCE: 19
GKATLTVDKS SSTAYMQLNS LTSEDSAVYY CAR                                              33

SEQ ID NO: 20           moltype = AA  length = 33
FEATURE                 Location/Qualifiers
source                  1..33
                        mol_type = protein
                        note = Sequence of heavy chain variable region in the CDR3
                         region of the humanized anti-tissue factor antibody MAb01
                        organism = synthetic construct
SEQUENCE: 20
GKGTLSLDHS TSTAYMELNS LRYEDTAVYF CAR                                              33

SEQ ID NO: 21           moltype = AA  length = 33
FEATURE                 Location/Qualifiers
source                  1..33
                        mol_type = protein
                        note = Sequence of heavy chain variable region in the CDR3
                         region of the humanized anti-tissue factor antibody MAb02
                        organism = synthetic construct
SEQUENCE: 21
AKATLSVDHS TSNAYMEINS LRYEDTAVYF CAR                                              33

SEQ ID NO: 22           moltype = AA  length = 8
FEATURE                 Location/Qualifiers
source                  1..8
                        mol_type = protein
                        note = Sequence of heavy chain variable region in the FR3
                         region before modification
                        organism = synthetic construct
SEQUENCE: 22
DVTTAVDF                                                                          8

SEQ ID NO: 23           moltype = AA  length = 8
FEATURE                 Location/Qualifiers
source                  1..8
                        mol_type = protein
                        note = Sequence of heavy chain variable region in the FR3
                         region of the humanized anti-tissue factor antibody MAb01
                        organism = synthetic construct
SEQUENCE: 23
DVTTALDF                                                                          8

SEQ ID NO: 24           moltype = AA  length = 8
FEATURE                 Location/Qualifiers
source                  1..8
                        mol_type = protein
                        note = Sequence of heavy chain variable region in the FR3
                         region of the humanized anti-tissue factor antibody MAb02
                        organism = synthetic construct
SEQUENCE: 24
DVTSALEF                                                                          8

SEQ ID NO: 25           moltype = AA  length = 11
FEATURE                 Location/Qualifiers
source                  1..11
                        mol_type = protein
                        note = Sequence of heavy chain variable region in the FR4
                         region before modification
```

```
                                    -continued

SEQUENCE: 25
WGQGTTLTVS S                                                        11

SEQ ID NO: 26           moltype = AA  length = 11
FEATURE                 Location/Qualifiers
source                  1..11
                        mol_type = protein
                        note = Sequence of heavy chain variable region in the FR4
                         region of the humanized anti-tissue factor antibody MAb01
                         or MAb02
                        organism = synthetic construct
SEQUENCE: 26
WGQGTSVTVS S                                                        11

SEQ ID NO: 27           moltype = AA  length = 23
FEATURE                 Location/Qualifiers
source                  1..23
                        mol_type = protein
                        note = Original sequence of light chain variable region in
                         the FR1 region
                        organism = synthetic construct
SEQUENCE: 27
DIQMTQSPSS LSASVGDRVT ITC                                           23

SEQ ID NO: 28           moltype = AA  length = 23
FEATURE                 Location/Qualifiers
source                  1..23
                        mol_type = protein
                        note = Sequence of light chain variable region in the FR1
                         region of the humanized anti-tissue factor antibody MAb01
                        organism = synthetic construct
SEQUENCE: 28
DIQMTQSPAS ISASIGERVT ITC                                           23

SEQ ID NO: 29           moltype = AA  length = 23
FEATURE                 Location/Qualifiers
source                  1..23
                        mol_type = protein
                        note = Sequence of light chain variable region in the FR1
                         region of the humanized anti-tissue factor antibody MAb02
                        organism = synthetic construct
SEQUENCE: 29
DIQMTQSPAS ISASVGERVT ITC                                           23

SEQ ID NO: 30           moltype = AA  length = 11
FEATURE                 Location/Qualifiers
source                  1..11
                        mol_type = protein
                        note = Original sequence of light chain variable region in
                         the CDR1 region
                        organism = synthetic construct
SEQUENCE: 30
LATQTLDTWL A                                                        11

SEQ ID NO: 31           moltype = AA  length = 11
FEATURE                 Location/Qualifiers
source                  1..11
                        mol_type = protein
                        note = Sequence of light chain variable region in the CDR1
                         region of the humanized anti-tissue factor antibody MAb01
                        organism = synthetic construct
SEQUENCE: 31
LASQTIDTWL A                                                        11

SEQ ID NO: 32           moltype = AA  length = 11
FEATURE                 Location/Qualifiers
source                  1..11
                        mol_type = protein
                        note = Sequence of light chain variable region in the CDR1
                         region of the humanized anti-tissue factor antibody MAb02
                        organism = synthetic construct
SEQUENCE: 32
LGSQTIDTYL A                                                        11

SEQ ID NO: 33           moltype = AA  length = 15
FEATURE                 Location/Qualifiers
source                  1..15
                        mol_type = protein
```

```
                        note = Original sequence of light chain variable region in
                           the FR2 region
                        organism = synthetic construct
SEQUENCE: 33
WYQQKPGKAP QLLIY                                                           15

SEQ ID NO: 34           moltype = AA  length = 6
FEATURE                 Location/Qualifiers
source                  1..6
                        mol_type = protein
                        note = Sequence of light chain variable region in the FR2
                           region of the humanized anti-tissue factor antibody MAb01
                        organism = synthetic construct
SEQUENCE: 34
WFLQKP                                                                      6

SEQ ID NO: 35           moltype = AA  length = 15
FEATURE                 Location/Qualifiers
source                  1..15
                        mol_type = protein
                        note = Sequence of light chain variable region in the FR2
                           region of the humanized anti-tissue factor antibody MAb02
                        organism = synthetic construct
SEQUENCE: 35
WYLQKPGRSP QLLIY                                                           15

SEQ ID NO: 36           moltype = AA  length = 7
FEATURE                 Location/Qualifiers
source                  1..7
                        mol_type = protein
                        note = Original sequence of light chain variable region in
                           the CDR2 region
                        organism = synthetic construct
SEQUENCE: 36
AATYLAD                                                                     7

SEQ ID NO: 37           moltype = AA  length = 7
FEATURE                 Location/Qualifiers
source                  1..7
                        mol_type = protein
                        note = Sequence of light chain variable region in the CDR2
                           region of the humanized anti-tissue factor antibody MAb01
                        organism = synthetic construct
SEQUENCE: 37
AATNLAD                                                                     7

SEQ ID NO: 38           moltype = AA  length = 7
FEATURE                 Location/Qualifiers
source                  1..7
                        mol_type = protein
                        note = Sequence of light chain variable region in the CDR2
                           region of the humanized anti-tissue factor antibody MAb02
                        organism = synthetic construct
SEQUENCE: 38
AATQLAD                                                                     7

SEQ ID NO: 39           moltype = AA  length = 32
FEATURE                 Location/Qualifiers
source                  1..32
                        mol_type = protein
                        note = Original sequence of light chain variable region in
                           the CDR3 region
                        organism = synthetic construct
SEQUENCE: 39
GVPSRFSGSG SGTDFTFTIS SLQPEDFATY YC                                         32

SEQ ID NO: 40           moltype = AA  length = 32
FEATURE                 Location/Qualifiers
source                  1..32
                        mol_type = protein
                        note = Sequence of light chain variable region in the CDR3
                           region of the humanized anti-tissue factor antibody MAb01
                        organism = synthetic construct
SEQUENCE: 40
GVPYRFSASG SGNDFSLTIS SLNPEDVATY YC                                         32

SEQ ID NO: 41           moltype = AA  length = 32
FEATURE                 Location/Qualifiers
source                  1..32
```

```
                                mol_type = protein
                                note = Sequence of light chain variable region in the CDR3
                                 region of the humanized anti-tissue factor antibody MAb02
                                organism = synthetic construct
SEQUENCE: 41
GVPSRFSASG SGTDFSLTIS SLQPEDVATY YC                                     32

SEQ ID NO: 42              moltype = AA  length = 9
FEATURE                    Location/Qualifiers
source                     1..9
                                mol_type = protein
                                note = Original sequence of light chain variable region in
                                 the FR3 region
                                organism = synthetic construct
SEQUENCE: 42
QLVYSSPST                                                                9

SEQ ID NO: 43              moltype = AA  length = 9
FEATURE                    Location/Qualifiers
source                     1..9
                                mol_type = protein
                                note = Sequence of light chain variable region in the FR3
                                 region of the humanized anti-tissue factor antibody MAb01
                                organism = synthetic construct
SEQUENCE: 43
QQVYSSPFT                                                                9

SEQ ID NO: 44              moltype = AA  length = 9
FEATURE                    Location/Qualifiers
source                     1..9
                                mol_type = protein
                                note = Sequence of light chain variable region in the FR3
                                 region of the humanized anti-tissue factor antibody MAb02
                                organism = synthetic construct
SEQUENCE: 44
QNVYSSPFT                                                                9

SEQ ID NO: 45              moltype = AA  length = 10
FEATURE                    Location/Qualifiers
source                     1..10
                                mol_type = protein
                                note = Original sequence of light chain variable region in
                                 the FR4 region
                                organism = synthetic construct
SEQUENCE: 45
FGQGTKLEIK                                                              10

SEQ ID NO: 46              moltype = AA  length = 10
FEATURE                    Location/Qualifiers
source                     1..10
                                mol_type = protein
                                note = Sequence of light chain variable region in the FR4
                                 region of the humanized anti-tissue factor antibody MAb01
                                organism = synthetic construct
SEQUENCE: 46
FGQGNKLEIR                                                              10

SEQ ID NO: 47              moltype = AA  length = 117
FEATURE                    Location/Qualifiers
source                     1..117
                                mol_type = protein
                                note = amino acid sequence of heavy chain variable region
                                 of humanized anti-tissue factor antibody
                                organism = synthetic construct
SEQUENCE: 47
QIQLVQSGPE LVKPGASVQV SCKTSGYSFT DYNVYWVRQS PAKGIEWIGY IDPYNGLTIY        60
EQNFRGKGTL SLDHSTSTAY MELNSLRYED TAVYFCARDV TTALDFWGQG TSVTVSS          117

SEQ ID NO: 48              moltype = AA  length = 107
FEATURE                    Location/Qualifiers
source                     1..107
                                mol_type = protein
                                note = amino acid sequence of light chain variable region
                                 of humanized anti-tissue factor antibody
                                organism = synthetic construct
SEQUENCE: 48
DIQMTQSPAS ISASIGERVT ITCLASQTID TWLAWFLQKP GRSPNLLIYA ATNLADGVPY        60
RFSASGSGND FSLTISSLNP EDVATYYCQQ VYSSPFTFGQ GNKLEIR                     107
```

| | | |
|---|---|---|
| SEQ ID NO: 49 | moltype = AA  length = 10 | |
| FEATURE | Location/Qualifiers | |
| source | 1..10<br>mol_type = protein<br>note = Sequence of light chain variable region in the FR4<br> region of the humanized anti-tissue factor antibody MAb02<br>organism = synthetic construct | |
| SEQUENCE: 49 | | |
| FGQGNKLEIK | | 10 |

What is claimed is:

1. An antibody-drug conjugate obtained by coupling a humanized anti-tissue factor antibody to a cytotoxic drug, wherein the humanized anti-tissue factor antibody comprises a heavy chain as set forth in SEQ ID NO: 3 and a light chain as set forth in SEQ ID NO: 4.

2. The antibody-drug conjugate according to claim 1, wherein the cytotoxic drug is at least one selected from the group consisting of a dolastatin derivative MMAE, an anti-tubulin inhibitor MMAF, a maytansinoid derivative DM1, and a DNA topoisomerase I inhibitor DX8951.

3. The antibody-drug conjugate according to claim 1, wherein the humanized anti-tissue factor antibody and the cytotoxic drug are coupled via a linker, wherein the linker cytotoxic drug is selected from the group consisting of MC-VC-PAB-MMAE, MC-VC-PAB-MMAF, MC-VC-PAB-DM1, MC-GGFG-DX8951, MC-SMCC-DM1; and
wherein a DAR value of the antibody-drug conjugate is 2-8.

4. A method for treating a tissue factor-positive cancer, comprising administering the antibody-drug conjugate according to claim 1 to a patient in need thereof.

5. The method according to claim 4, wherein the antibody-drug conjugate is administered in combination with an additional anti-cancer drug.

6. The method according to claim 4, wherein the tissue factor-positive cancer is at least one selected from the group consisting of ovarian cancer, non-small cell lung cancer, adenocarcinoma in situ, bowel cancer, cervical cancer, prostate cancer, endometrial cancer, pancreatic cancer, esophageal cancer, bladder cancer, gastric cancer, liver cancer, colon cancer, and breast cancer.

7. The method according to claim 4, wherein the cytotoxic drug is at least one selected from the group consisting of a dolastatin derivative MMAE, an anti-tubulin inhibitor MMAF, a maytansinoid derivative DM1, and a DNA topoisomerase I inhibitor DX8951.

8. The method according to claim 5, wherein the additional anti-cancer drug comprises gemcitabine.

9. The method according to claim 6, wherein the antibody-drug conjugate is administered in combination with an additional anti-cancer drug.

10. The method according to claim 9, wherein the additional anti-cancer drug comprises gemcitabine.

* * * * *